US011131646B2

(12) United States Patent
Johnson et al.

(10) Patent No.: US 11,131,646 B2
(45) Date of Patent: Sep. 28, 2021

(54) ELECTROCHEMICAL SEQUENCING OF DNA USING AN EDGE ELECTRODE

(71) Applicant: Robert Bosch GmbH, Stuttgart (DE)

(72) Inventors: Christopher Johnson, San Carlos, CA (US); Habib Ahmad, Sunnyvale, CA (US); Nadezda Fomina, Redwood City, CA (US); Gary Yama, Mountain View, CA (US); Franz Laermer, Weil Der Stadt (DE); Jochen Hoffmann, Renningen (DE); Patrick Staley, Sunnyvale, CA (US); Christoph Lang, Cupertino, CA (US); Young Shik Shin, Mountain View, CA (US)

(73) Assignee: ROBERT BOSCH GMBH, Stuttgart (DE)

(*) Notice: Subject to any disclaimer, the term of this patent is extended or adjusted under 35 U.S.C. 154(b) by 285 days.

(21) Appl. No.: 16/009,766

(22) Filed: Jun. 15, 2018

(65) Prior Publication Data
US 2019/0137435 A1    May 9, 2019

Related U.S. Application Data

(60) Provisional application No. 62/581,366, filed on Nov. 3, 2017.

(51) Int. Cl.
| | | |
|---|---|---|
| *G01N 27/327* | (2006.01) | |
| *G01N 33/487* | (2006.01) | |
| *C12Q 1/6869* | (2018.01) | |
| *C12Q 1/6825* | (2018.01) | |

(52) U.S. Cl.
CPC ....... *G01N 27/3277* (2013.01); *C12Q 1/6825* (2013.01); *C12Q 1/6869* (2013.01); *G01N 27/3278* (2013.01); *G01N 33/48721* (2013.01)

(58) Field of Classification Search
None
See application file for complete search history.

(56) References Cited

U.S. PATENT DOCUMENTS

| | | |
|---|---|---|
| 7,939,259 B2 | 5/2011 | Kokoris et al. |
| 8,324,360 B2 | 12/2012 | Kokoris et al. |
| 8,349,565 B2 | 1/2013 | Kokoris et al. |

(Continued)

OTHER PUBLICATIONS

Goodwin et al., "Coming of age: ten years of next-generation sequencing technologies," Nature Reviews Genetics 17, 333-351 (2016).

(Continued)

*Primary Examiner* — J. Christopher Ball
(74) *Attorney, Agent, or Firm* — Norton Rose Fulbright US LLP; Gerard Messina

(57) ABSTRACT

A device to electrochemically sequence DNA that includes a redox species includes at least one edge electrode, at least one stack of insulator material, and a pair of DNA translocation electrodes including a DNA translocation working electrode and a DNA translocation counter electrode, where the thickness of the at least one edge electrode is about 0.5 nanometers, and the thickness of the at least one stack of insulator material is about 10 nanometers. Methods of electrochemically sequencing a strand of DNA are also provided.

21 Claims, 19 Drawing Sheets
(18 of 19 Drawing Sheet(s) Filed in Color)

(56) References Cited

U.S. PATENT DOCUMENTS

| | | | | |
|---|---|---|---|---|
| 2010/0327874 | A1* | 12/2010 | Liu | G01N 27/44791 324/464 |
| 2012/0193231 | A1* | 8/2012 | Afzali-Ardakani | G01N 33/48721 204/451 |
| 2012/0288948 | A1* | 11/2012 | Lindsay | G01N 33/48721 436/94 |
| 2014/0326604 | A1* | 11/2014 | Han | G01N 33/48721 204/543 |
| 2015/0028845 | A1* | 1/2015 | Zhu | G01N 33/48721 324/71.5 |

OTHER PUBLICATIONS

Drummond et al., "Electrochemical DNA Sensors," Nature Biotechnology 21, 1192-1199 (2003).

Debela et al., Chem Commum 52, 757 (2016).

Emil Paleček et al., "Electrochemistry of Nucleic Acids," Institute of Biophysics, Academy of Sciences of the Czech Republic, Chem. Rev., 112(6), pp. 3427-3481 (2012).

Hocek et al., "Nucleobase modification as redox DNA labelling for electrochemical detection," Chem. Soc. Rev., 40, 5802-5814 (2011).

George, "Atomic Layer Deposition: An Overview," Chem. Rev. 110(1), pp. 111-131 (2010).

Langereis et al., "In situ spectroscopic ellipsometry study on the growth of ultrathin TiN films by plasma-assisted atomic layer deposition," J. Appl. Phys. 100, 023534 (2006).

Kim et al., "Large-scale pattern growth of graphene films for stretchable transparent electrodes," Nature, 457, 706-710 (2009).

Hocek, "Synthesis of Base-Modified 2'-Deoxyribonucleoside Inphosphates and Their Use in Enzymatic Synthesis of Modified DNA for Applications in Bioanalysis and Chemical Biology," J. Org. Chem., 79(21), pp. 9914-9921 (2014), p. 9914-9921 October.

Carson et al., "Challenges in DNA motion control and sequence readout using nanopore devices," Nanotechnology, 26(7):074004 (2015), paper No. 074004; 24 pages February.

Sørensen et al., Automation of a single-DNA molecule stretching device, Review of Scientific Instruments, 2015, paper No. 063702; 7 pages June.

Pud et al., Mechancial trapping of DNA in a Double-Nanopore System, Nano Lett. 2016, p. 8021-8028 December.

* cited by examiner

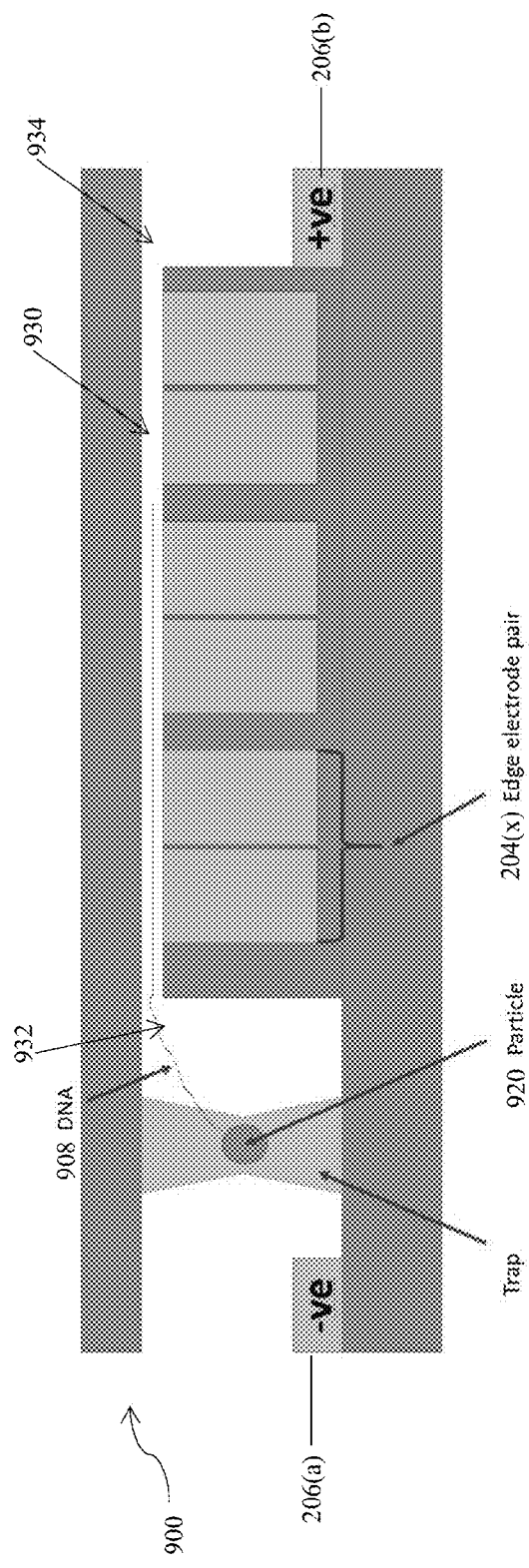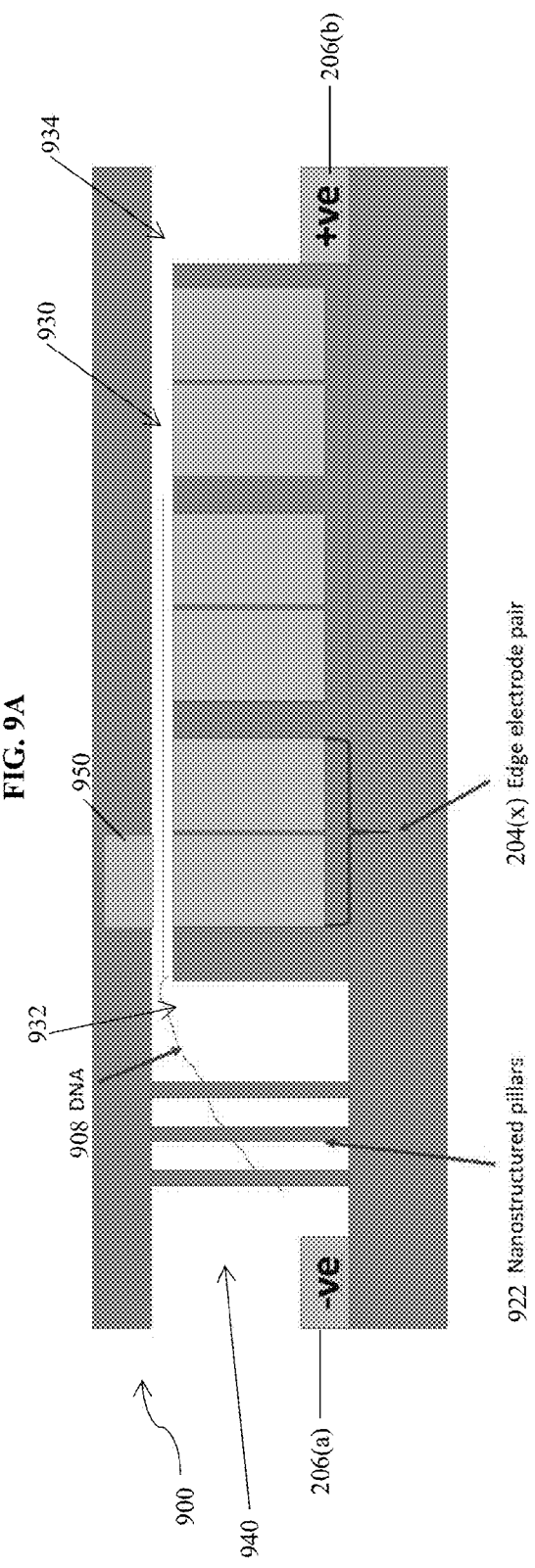
FIG. 9A
FIG. 9B

ELECTROCHEMICAL SEQUENCING OF DNA USING AN EDGE ELECTRODE

CROSS-REFERENCE TO RELATED APPLICATION

The present application claims the benefit, under 35 U.S.C. § 119(e), of U.S. Provisional Pat. App. Ser. No. 62/581,366 filed Nov. 3, 2017.

FIELD OF THE INVENTION

Aspects of the present invention relate to a method for sequencing of polynucleotides.

BACKGROUND

There are currently many designs for devices aimed at real time sequencing of DNA. See, e.g., Goodwin et al., "Coming of age: ten years of next-generation sequencing technologies," Nature Reviews Genetics 17, 333-351 (2016); and Drummond et al., "Electrochemical DNA Sensors," Nature Biotechnology 21, 1192-1199 (2003). Some gene sequencing technologies involve short read lengths in the order of 100s of bp reads of base pairs (bp), thus requiring significant gene reconstruction post processing to generate the final sequence.

One technology that has garnered significant attention is the detection of DNA electronically, as this enables translation of the DNA directly into a digital output without requiring complicated optics currently employed in fluorescence-based sequencing techniques. Electronic readout leverages the highly reproducible miniaturization techniques employed within the microelectronics industry. The primary modality of detecting DNA electronically is the nanopore concept, where DNA translocation through a nanopore is monitored as a change in resistivity dependent on the DNA base(s) occupying the pore.

Some have incorporated redox modified nucleotides and used electrochemistry as a method to probe DNA. See, e.g., Debela et al., Chem Commun 52, 757 (2016) ("Debela"); Emil Paleček et al., "Electrochemistry of Nucleic Acids," Institute of Biophysics, Academy of Sciences of the Czech Republic, Chem. Rev., 112(6), pp. 3427-3481 (2012) ("Paleček"); and Hocek et al., "Nucleobase modification as redox DNA labelling for electrochemical detection," Chem. Soc. Rev., 40, 5802-5814 (2011). However, there is currently no technology that allows real-time single base resolution redox sequencing. One significant issue with detecting a redox species is the scale of the electrode. If the electrode is too large, then the electrode will simultaneously interact with multiple redox species, preventing discrimination at the single base level. Fabrication of the scale of the electrode required to address bases with single base resolution is a challenge.

With the advent of technologies such as atomic layer deposition (ALD) (see George, "Atomic Layer Deposition: An Overview," Chem. Rev. 110(1), pp. 111-131 (2010) ("George") and Langereis et al., "In situ spectroscopic ellipsometry study on the growth of ultrathin TiN films by plasma-assisted atomic layer deposition," J. Appl. Phys. 100, 023534 (2006)) and graphene chemical vapor deposition (Kim et al., "Large-scale pattern growth of graphene films for stretchable transparent electrodes," Nature, 457, 706-710 (2009)), it is possible to achieve sub-nanometer thick electrodes and to generate an electrode edge on the same scale as the species being probed. See, e.g., George.

Redox chemistry is a well understood property within electrochemistry, and modification of nucleobases with redox species has been demonstrated within the literature previously. See, e.g., Hocek, "Synthesis of Base-Modified 2'-Deoxyribonucleoside Triphosphates and Their Use in Enzymatic Synthesis of Modified DNA for Applications in Bioanalysis and Chemical Biology," J. Org. Chem., 79 (21), pp. 9914-9921 (2014) ("Hocek 2014"). Either the sugar, phosphate, or nucleobase itself can be modified with redox functional species.

The principal of introducing a sequence between bases is described in U.S. Pat. Nos. 7,939,259, 8,324,360, and 8,349,565, where a coding region is introduced between DNA bases that correlate to the base insertion. Specifically, an Xpandomer sequence is used to incorporate an expansion of a DNA sequence for probing with a nanopore using the change in resistance as the DNA travels through the pore to measure the DNA bases.

SUMMARY

A summary of certain example embodiments of the present invention is set forth below. It should be understood that these aspects are presented merely to provide the reader with a brief summary of these certain embodiments and that these aspects are not intended to limit the scope of the present invention. Indeed, this invention can encompass a variety of aspects that may not be set forth below.

Example embodiments of the present invention combine the principle of modifiability of nucleotides with redox species, with nanoscale fabrication techniques and DNA linearization techniques, to electrochemically sequence strands of polynucleotides, including strands of DNA.

Example embodiments of the present invention integrate a nanoscale edge electrode and linearized and electrochemically labeled DNA as a method to sequence DNA using electrochemistry. Unlike other gene sequencing technologies, the example embodiments of the present invention provide the ability to have long read lengths on the order of 1000s of base pairs (bp), providing a linear sequence readout of a strand of DNA in real time. Unlike nanopore DNA sequencing technology, the planar fabrication method allows for multiple edge electrode stack structures to be fabricated within a single reading device. This allows the same strand of DNA to be probed by multiple electrodes within the same reading run, enabling improved redundancy of the readout and thus improved accuracy of sequencing. Use of spacers to integrate a noncoding, non-redox region of DNA or other polymeric material between the electrochemically modified DNA to isolate the electrochemical groups as they pass over the electrode can be used to improve single base resolution.

Example embodiments of the present invention use atomic layer deposition and graphene chemical vapor deposition technologies to create an electrode edge and/or insulator layer on the same scale as the species being probed. The process is also compatible with current microfabrication protocols and is accurate and reproducible. According to example embodiments, by controlling the trajectory of the DNA through defined structural topology, a device is fabricated to ensure that a DNA travels in proximity to an electrode, such that bases are sequentially electrochemically addressable to give single base resolution. In a preferred example, the proximity is in a range of 0 nm to about 10 nm.

According to example embodiments, a device to electrochemically sequence DNA comprising a redox species includes: (a) at least one edge electrode; (b) at least one stack of insulator material; and (c) a pair of DNA translocation electrodes, the electrodes including a DNA translocation working electrode and a DNA translocation counter electrode, where the thickness of the at least one edge electrode is about 0.5 nanometers and the thickness of the at least one stack of insulator material is about 10 nanometers.

In some example embodiments, the device includes 1 to 50 edge electrodes and 1 to 50 stacks of insulator material, where the edge electrodes and stacks of insulator material alternate and the total thickness of the edge electrodes and stacks of insulator material is about 20 nanometers to about 1000 nanometers. In some advantageous example embodiments, the device includes, more specifically, 10 to 50 edge electrodes and 10 to 50 stacks of insulator material, where the edge electrodes and stacks of insulator material alternate and the total thickness of the edge electrodes and stacks of insulator material is about 105 nanometers to about 1000 nanometers.

In some example embodiments, the at least one edge electrode comprises a conductive material, and the insulator material comprises a dielectric material.

In some example embodiments, the at least one edge electrode is titanium nitride or platinum, and the insulator material is selected from the group consisting of silicon dioxide, silicon nitride, and aluminum oxide.

In some example embodiments, the at least one edge electrode and the insulator material are micro-structured or nano-structured by a suitably appropriate micro- or nano-fabrication structuring technique, for example, by dry etching, wet etching, reactive ion etching, lift off, chemical mechanical polishing, or ion beam milling processes.

According to example embodiments, a device to electrochemically sequence DNA comprising a redox species includes: (a) at least one pair of edge electrodes, the pair including a first electrode held at a oxidizing bias and a second electrode held at a reducing bias; (b) at least one stack of insulator material; and (c) a pair of DNA translocation electrodes, the pair including a DNA translocation working electrode and a DNA translocation counter electrode, where the first electrode and the second electrode are separated by an insulating layer, and above the insulating layer is a sensing zone within which a redox species can simultaneously be oxidized by the first electrode and reduced by the second electrode.

In some example embodiments, the device includes multiple pairs of edge electrodes, where at least any two pairs of edge electrodes are configured to measure or set a speed of translocation of the DNA across the multiple pairs of edge electrodes.

In some example embodiments, the speed of translocation of the DNA across the multiple pairs of edge electrodes is uniform.

In some example embodiments, the speed of translocation of the DNA across the multiple pairs of edge electrodes changes at a constant rate.

According to example embodiments, a method of electrochemically sequencing a strand of DNA includes: (a) modifying each nucleotide of at least two nucleotide base groups of the strand of DNA to incorporate a redox species; (b) applying a voltage to at least one edge electrode; (c) passing the strand of DNA over the at least one edge electrode; (d) oxidizing or reducing, using the at least one edge electrode, each modified nucleotide as each passes over the at least one edge electrode, where the oxidizing or reducing generates an electrochemical signal comprising a change in current; (e) identifying each modified nucleotide based on the electrochemical signal; and (f) determining a sequence of the strand of DNA, where each nucleotide of a first nucleotide base group has been modified to incorporate a first redox species having a first oxidation or reduction potential, and each nucleotide of a second nucleotide base group has been modified to incorporate a second redox species having a second oxidation or reduction potential.

In some example embodiments, the first and second nucleotide base groups are different, and the first and second nucleotide base groups are not complementary to each other.

In some example embodiments, the method further includes incorporating the redox modified nucleotides using polymerase chain reaction, multiple displacement amplification, or isothermal amplification.

In some example embodiments, the method further includes inserting a spacer between adjacent nucleotides of the strand of DNA.

In some example embodiments, applying the voltage to the at least one edge electrode includes cycling the voltage from an oxidation potential to a reducing potential.

In some example embodiments, each modified nucleotide is oxidized or reduced multiple times as each passes over the at least one edge electrode.

In some example embodiments, the method further includes passing the strand of DNA over multiple edge electrodes that are spaced at regular distances in parallel, where the sequence of the strand of DNA is determined multiple times using each edge electrode.

According to example embodiments, a method of electrochemically sequencing a strand of DNA includes: (a) modifying each nucleotide of the amplified strands of DNA to incorporate a redox species, where each modified nucleotide in a first group consists of a first nucleotide base, and each modified nucleotide in a second group consists of a second nucleotide base; (b) amplifying the modified strands of DNA; (c) applying a voltage to at least one edge electrode; (d) passing the amplified strands of DNA over the at least one edge electrode; (e) oxidizing or reducing, using the at least one edge electrode, each modified nucleotide as each passes over the at least one edge electrode, where the oxidizing or reducing generates an electrochemical signal includes a change in current; (f) overlaying the electrochemical signals generated from each amplified strand of DNA; (g) identifying each modified nucleotide; and (h) determining a sequence of the strand of DNA, where each modified nucleotide of the first group has been modified to incorporate the redox species, and each nucleotide of the second group has been modified to incorporate the redox species; where the first and second nucleotide bases are different and non-complementary.

In some example embodiments, the method further includes amplifying the strand of DNA prior to modifying each nucleotide of the strand of DNA to incorporate a redox species.

In some example embodiments, the method further includes ligating a known strand of DNA to each amplified strand of DNA;

In some example embodiments, the method further includes introducing a spacer between adjacent nucleotides of each amplified strand of DNA.

In some example embodiments, each modified nucleotide in a first group is either a redox modified Adenine or Thymine deoxynucleoside triphosphate (dNTP), and each modified nucleotide in a second of the groups is either a redox modified Cytosine or Guanine dNTP.

Although various aspects of the example embodiments of the present invention may be described independently, combinations of the example embodiments are understood to be referred to herein. In addition, and conversely, it should be understood that although a feature may be described in the context of a combination with other features, the different features are separable and do not necessarily require or rely on one another for a functional or useful embodiment of the present invention.

The aspects described in the foregoing are presented merely to provide a brief summary of these example embodiments, and these aspects are not intended to limit the scope of this disclosure. Indeed, the present invention may also encompass a variety of other aspects. These and other features, aspects, and advantages of the present invention are further clarified by the following detailed description of certain exemplary embodiments in view of the accompanying drawings throughout which like characters represent like parts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9A-9D illustrates methods of translocating a strand of DNA, according to example embodiments of the present invention.

DETAILED DESCRIPTION

Example embodiments of the present invention provide a DNA sequencing platform that can readout in real time the genetic sequence of a strand of DNA of any length, with minimal requirement for data post processing. This can be achieved using electrochemical techniques that can be translated into digital format, e.g., using multiple sampling to improve data fidelity and methods that are scalable for manufacturing. Example embodiments of the present invention use the modification of DNA with redox-active species, a novel microfabrication method to pattern nanoscale planar electrode edge structures, and/or a method to control the translocation of DNA across the nanoscale electrode edge structures.

Figure 1:
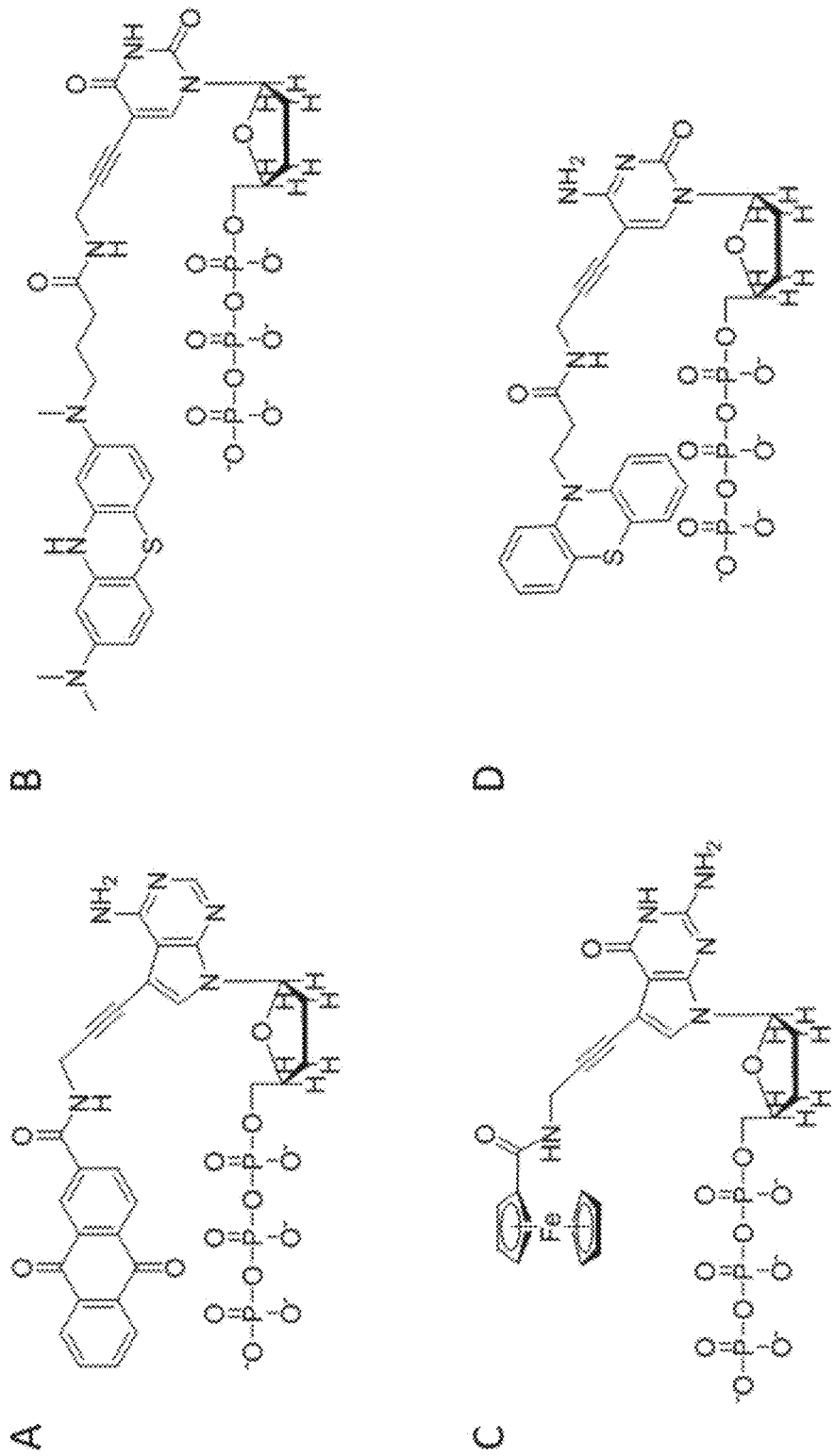
FIG. 1 shows a reproduction from Debela of the chemical structure of redox active dideoxy nucleotide triphosphates used for electrochemical primer extension assays (AQ: anthraquinone (0.40 V), MB: methylene blue (0.20 V), Fc: ferrocene (0.50 V), and PTZ: phenothiazine (0.60 V)), with all potentials vs. Ag/AgCl.
Figure 2:
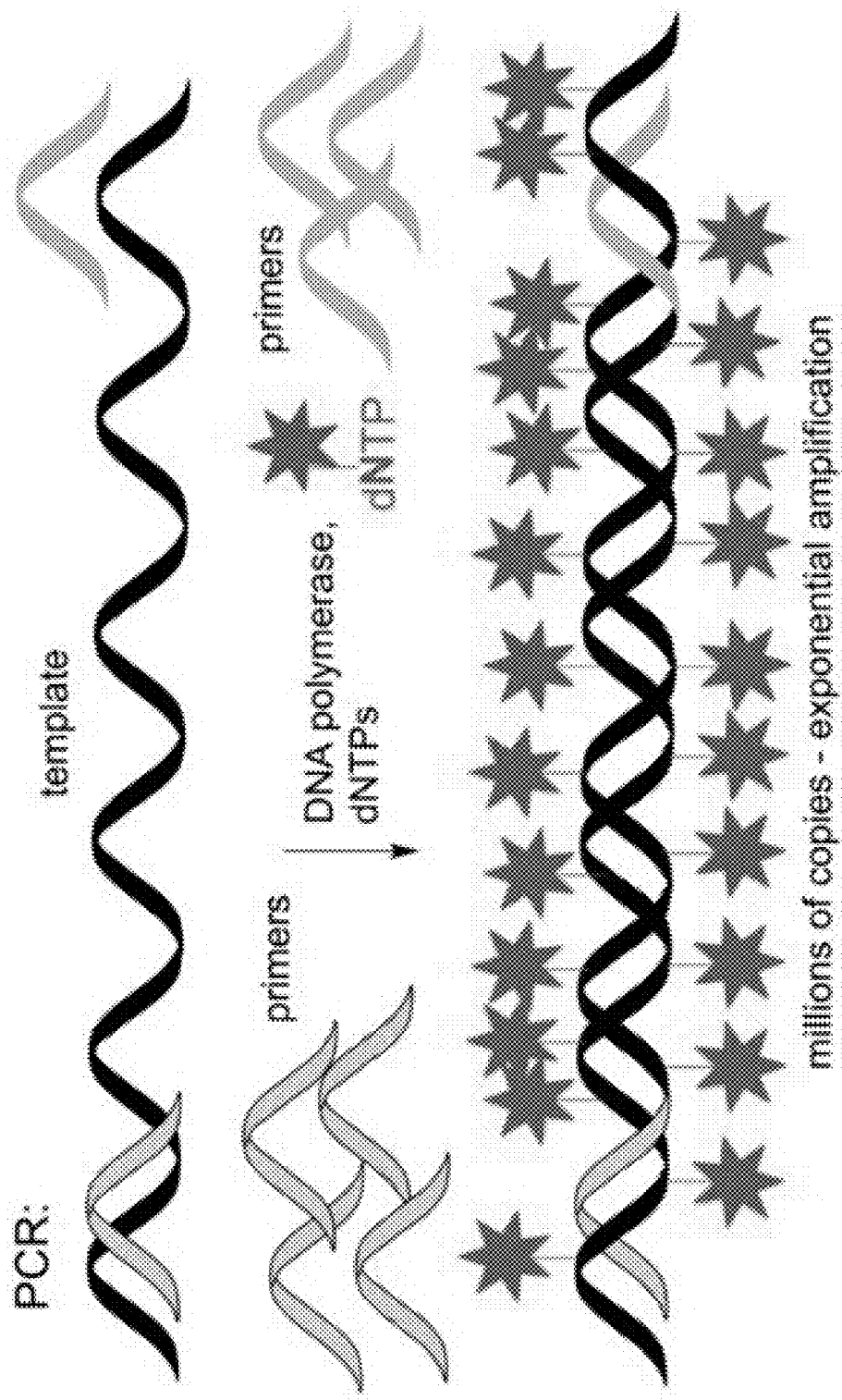
FIG. 2 is a schematic of incorporation of a redox modified dNTP (Red) into a DNA strand by PCR, reproduced from Hocek 2014.
Figure 3:
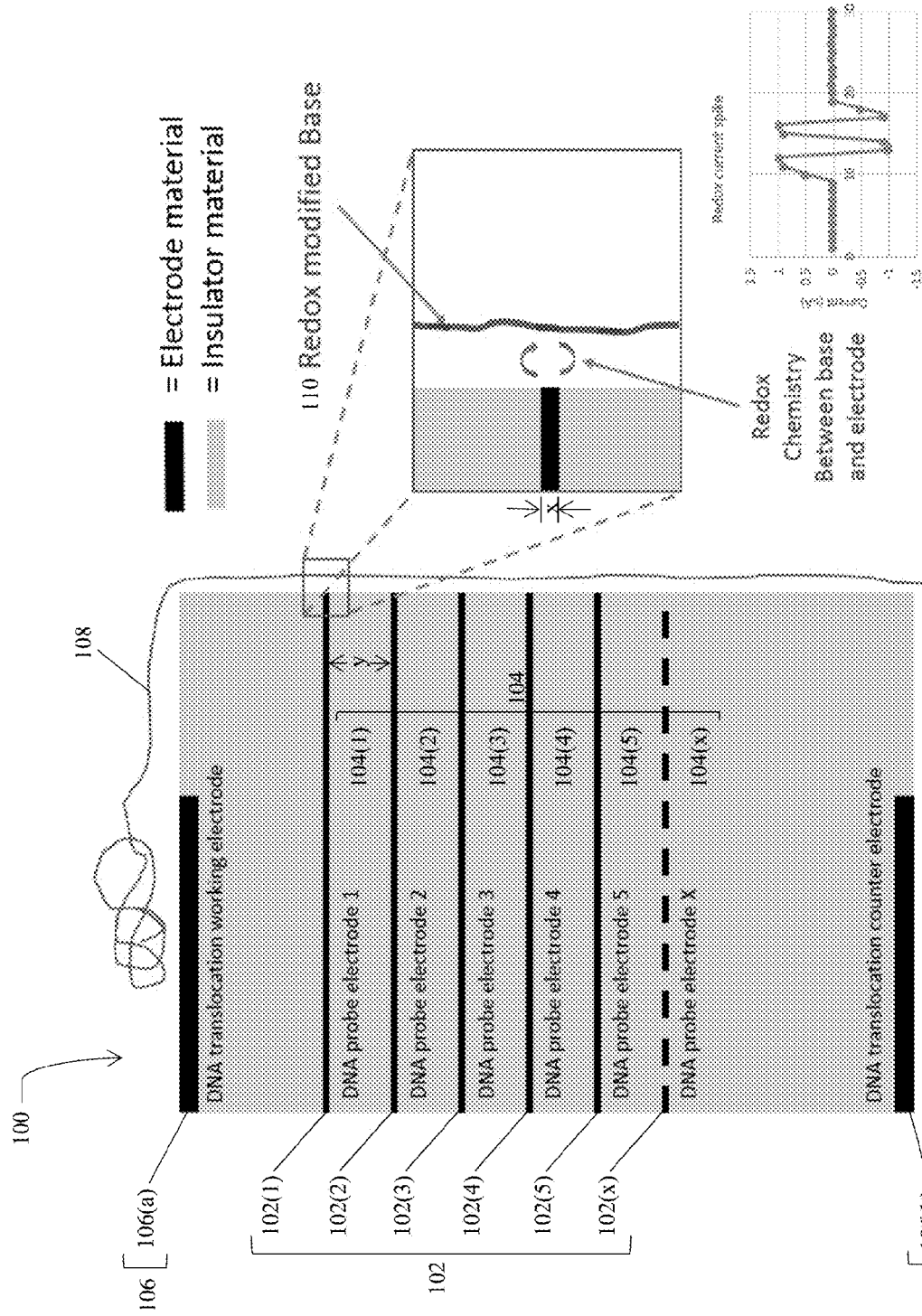
FIG. 3 illustrates a cross sectional schematic of a device according to an example embodiment of the present invention.

FIG. 3 shows device 100 that includes edge electrode 102(1), stack of insulator material 104(1), and a pair of DNA translocation electrodes 106 including DNA translocation working electrode 106($a$) and DNA translocation counter electrode 106($b$). In an example embodiment, the thickness x of edge electrode 102(1) is about 0.5 nanometers, and the thickness y of stack of insulator material 104(1) is about 10 nanometers (for proper insulation and reduction of cross-talk between electrode-layers). In an example embodiment, device 100 includes a reference electrode.

As shown in FIG. 3, device 100 can include multiple edge electrodes 102 (102(1), 102(2), 102(3), 102(4), 102(5), ... 102($x$)) that are fabricated at regular distances, and also multiple stacks of insulator material 104 (104(1), 104(2), 104(3), 104(4), 104(5), ... 104($x$)). As shown in FIG. 3, edge electrodes 102 and stacks of insulator material 104 alternate. According to an example embodiment, device 100 includes a sequence of 2 to 100 ALD-layer pairs, or 1 to 50 edge electrodes 102 and 1 to 50 stacks of insulator material 104, and with the thickness x of each edge electrode 102 at about 0.5 nanometers, and the thickness y of each stack of insulator material 104 at about 10 nanometers, the total thickness of edge electrodes 102 and stacks of insulator material 104 is about 20 nanometers to about 1000 nanometers. In an example embodiment, edge electrode 102 is made of a conductive material, such as titanium nitride or platinum. In an example embodiment, stack of insulator material 104 is made of a dielectric material, such as silicon dioxide, silicon nitride, or aluminum oxide. According to an example embodiment, stack of insulator material 104 and edge electrode 102 are controlled by precision deposition via ALD.

As shown in FIG. 3, strand of DNA 108 is translocated from the top of device 100 to the bottom of device 100, and thus translocates across each of edge electrodes 102. Such translocation can be achieved by applying a voltage bias on the pair of DNA translocation electrodes 106, or by applying a shuttling bias on edge electrodes 102. As each redox modified nucleotide base 110 of strand of DNA 108 passes over each of edge electrodes 102, a redox chemical reaction occurs between the redox modified nucleotide base 110 and edge electrode 102. According to an example embodiment, use of multiple electrodes spaced at regular distances allows strand of DNA 108 to be probed multiple times, and because the space between nucleotide bases is well characterized, the resulting signals can be overlaid and averaged to improve accuracy. According to an example embodiment, the speed of translocation of strand of DNA 108 across edge electrodes 102 is uniform, and is set to be slow enough to generate a readable signal and fast enough to ensure a rapid DNA sequencing test. According to an example embodiment, the speed of translocation of strand of DNA 108 is set by at least any two pairs of edge electrodes, such as the first two edge electrodes 102(1) and 102(2). These two pairs of edge electrodes, the first two edge electrodes 102(1) and 102(2) in this case, measure or set the speed of translocation of strand of DNA 108, then through a feedback mechanism, control and modulate the voltage of pair of DNA translocation electrodes 106 to either strengthen or weaken the electric field in order to regulate the speed of translocation of strand of DNA 108. According to an example embodiment, strand of DNA 108 can be linearized by confining it into a nanochannel, by using hydrodynamic forces, by a pore technique to pull strand of DNA 108 close to the surface, or by an electrical charge-based method including surface modification or an additional electrode on the nanochannel surface. While FIG. 3 illustrates a vertical structure, the present invention can also be a planar structure.

According to an example embodiment, edge electrodes 102 operate a cyclic voltammetric measurement resulting in a current spike as a redox active base interacts with the electrode 102 as it traverses over the edge. According to an example embodiment, rapid cycling of the oxidation or reduction potentials occurs at edge electrodes 102, such that multiple cycles of oxidation or reduction are applied to probed strand of DNA 108; and if there is more than one nucleotide base being probed, observation of the electrochemical signal transients will improve the deconvolution of the base sequence.

According to an example embodiment, the edge electrode 102 and stack of insulator material 104 are micro-structured by dry etching, wet etching, reactive ion etching, lift off, chemical mechanical polishing, ion beam milling processes, or any other micro- or nano-fabrication structuring technique. Both selective and non-selective chemistries can be used (e.g., $SF_6$ is selective to TiN; ion beam milling is non-selective to TiN, etc.). In addition, there are selective wet-etchants available for TiN ($NH_4OH$, $H_2O_2$, $H_2O$) and $SiO_2$ (buffered HF), respectively.

According to an example embodiment, structuring after deposition of the multilayer on top of a silicon surface is performed as follows:

Photomask and Plasma etch through the whole multilayer stack to define a narrow long tongue on one end and a wide contact area at the other end (non-selective ion beam milling is used to make it through the multilayer in one single etch), for defining the devices' geometries and devices' separation from each other;

Apply liquid selective Ti-etch ($NH_4OH$, $H_2O_2$, $H_2O$) to recess the Ti metal from all sides (i.e., underetch the $SiO_2$-layers for a certain distance from the edges), so that no electrical contacts are open to the environment at any sidewall;

Deposit a final $SiO_2$ ALD-coating of about 10 to 100 nm thickness to close the $SiO_2^-$ layers sides (passivate and seal the open TiN-layers from the environment at all sidewalls);

Sequentially mask and etch $SiO_2$ and TiN in the contact area, to define and open TiN-contact pad by TiN-contact pad one after another at increasing layer depths (selective plasma etches: $SF_6$ for TiN and $CHF_3$, $CF_4$, Ar for $SiO_2$ with etch-stop on TiN; or liquid etches $NH_4OH$, $H_2O_2$, $H_2O$ for TiN, buffered HF for $SiO_2$) (several alternatives for sequential masking and etching are well-known in the art), whereby, in the end, all TiN-layers have one open contact pad each for electrical connection in the contact area of the device;

Photomask and ion beam mill through the front end of the "tongue," through the whole multilayer stack, to re-open the TiN-layers that are along the one particular sidewall, resulting in the "DNA sampling area";

Glue a carrier foil on top of the multilayer system (covering all devices), pull them off the PorSi-separator, and copy them device-by-device to Lab-on-Chips; and Provide the electrical connection to the Ti contact pads on the Lab-on-Chips (e.g., by flex-foil interconnection technologies).

According to example embodiments, the electrical attraction of the DNA to the sampling sidewall, transport along the sampling sidewall, and readout at the sampling sidewall is performed by "travelling electrical waves" or "switched electrical potentials in a travelling wave logic" along the TiN layers, combined with current sampling.

According to example embodiments, redox species are incorporated that correlate to the target DNA strand to be sequenced. According to an example embodiment, a polymerase is used to integrate the corresponding redox modified DNA with high fidelity during amplification. According to an example embodiment, Polymerase Chain Reaction (PCR), multiple displacement amplification, isothermal Amplification, or any other method to replicate a target strand of DNA that can incorporate one or more redox modified base with high fidelity is used. For example, B-family thermostable polymerases can be used (Vent (exo-), Pwo, KOD) as enzymes that will tolerate incorporation of the modified nucleotide. See, e.g., Paleček.

Figure 4A:
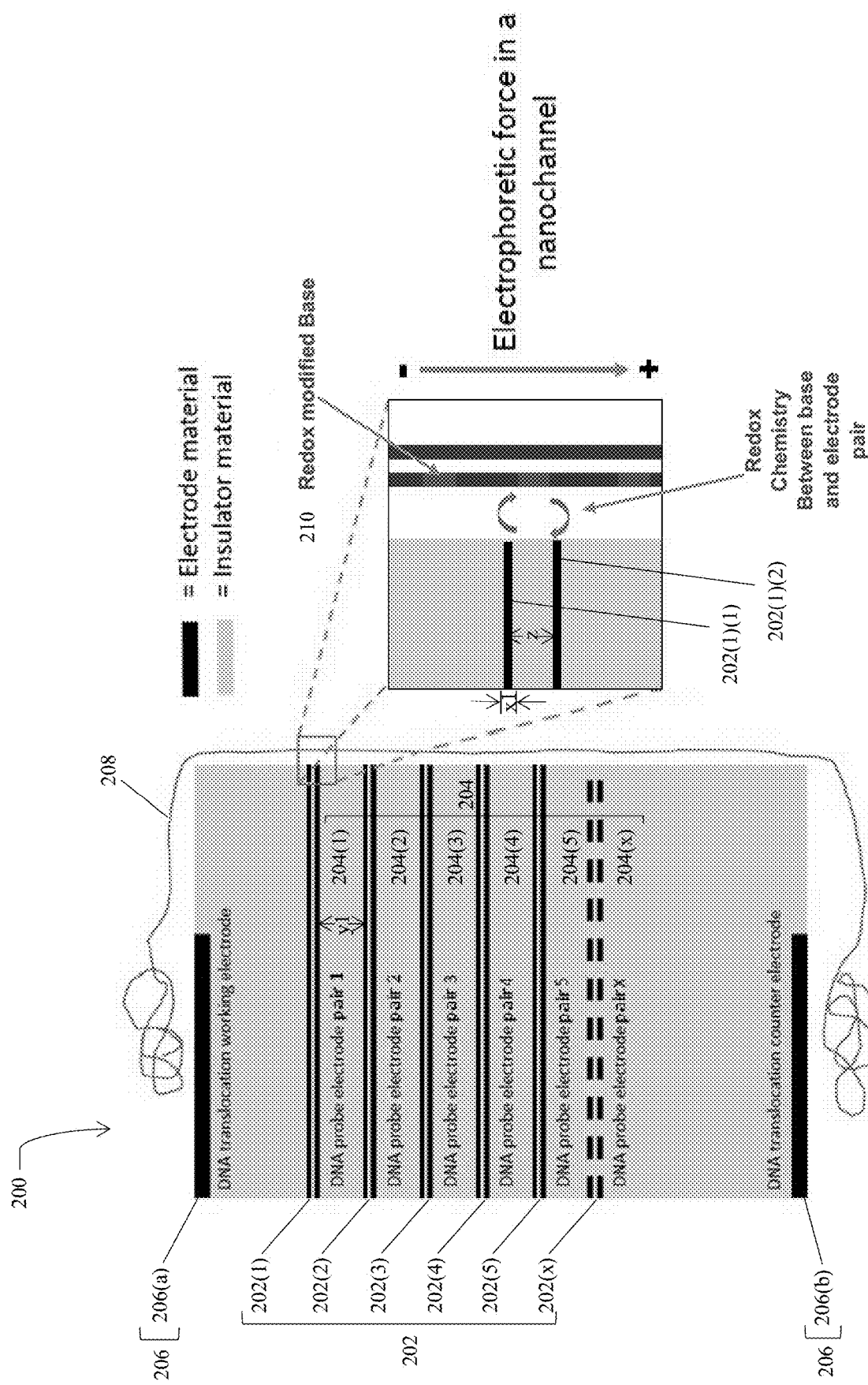
FIG. 4A illustrates a cross sectional schematic of a device according to an alternative example embodiment of the present invention.

FIG. 4A shows device 200 that includes edge electrode pair 202(1), stack of insulator material 204(1), and a pair of DNA translocation electrodes 206 including DNA translocation working electrode 206(a) and DNA translocation counter electrode 206(b). Edge electrode pair 202(1) includes first electrode 202(1)(1) and second electrode 202(1)(2) separated by insulating layer z. In an example embodiment, the thickness x1 of edge electrode 201(1)(a) is about 50 nanometers, the thickness y1 of stack of insulator material 204(1) is greater than about 10 nanometers (for proper insulation and reduction of cross-talk between electrode pair-layers), and the thickness of insulating layer z is about 0.1 nanometers to about 10 nanometers. In an example embodiment, device 200 includes a reference electrode.

As shown in FIG. 4A, device 200 can include multiple edge electrode pairs 202 (202(1), 202(2), 202(3), 202(4), 202(5), . . . 202(x)) that are fabricated at regular distances, where each edge electrode pair includes first electrode 202(x)(1) and second electrode 202(x)(2) separated by insulating layer z. Device 200 can thus also include multiple stacks of insulator material 204 (204(1), 204(2), 204(3), 204(4), 204(5), . . . 204(x)). As shown in FIG. 4A, edge electrode pairs 202 and stacks of insulator material 204 alternate. According to an example embodiment, device 200 includes a sequence of 20 to 100 electrodes, or 10 to 50 edge electrode pairs 202 and 10 to 50 stacks of insulator material 204, and with the thickness x1 of each electrode in electrode pair 202 at about 50 nanometers, the thickness of insulating layer z at about 0.1 nanometers to about 10 nanometers, and the thickness y1 of each stack of insulator material 204 at greater than about 10 nanometers, the total thickness of edge electrode pairs 202 and stacks of insulator material 204 is about 1200 nanometers to about 6000 nanometers. In an example embodiment, edge electrode pair 202 is made of a conductive material, such as titanium nitride or platinum, and stack of insulator material 204 is made of a dielectric material, such as silicon dioxide, silicon nitride, or aluminum oxide. According to an example embodiment, deposition of insulating layer z is controlled by precision deposition via ALD.

As shown in FIG. 4A, strand of DNA 208 is translocated from the top of device 200 to the bottom of device 200, and thus translocates across each of edge electrode pairs 202. Such translocation can be achieved by applying a voltage bias on the pair of DNA translocation electrodes 206, or by applying a shuttling bias on edge electrode pairs 202. While FIG. 4A illustrate a vertical structure, the present invention can also be a planar structure.

Figure 4B:
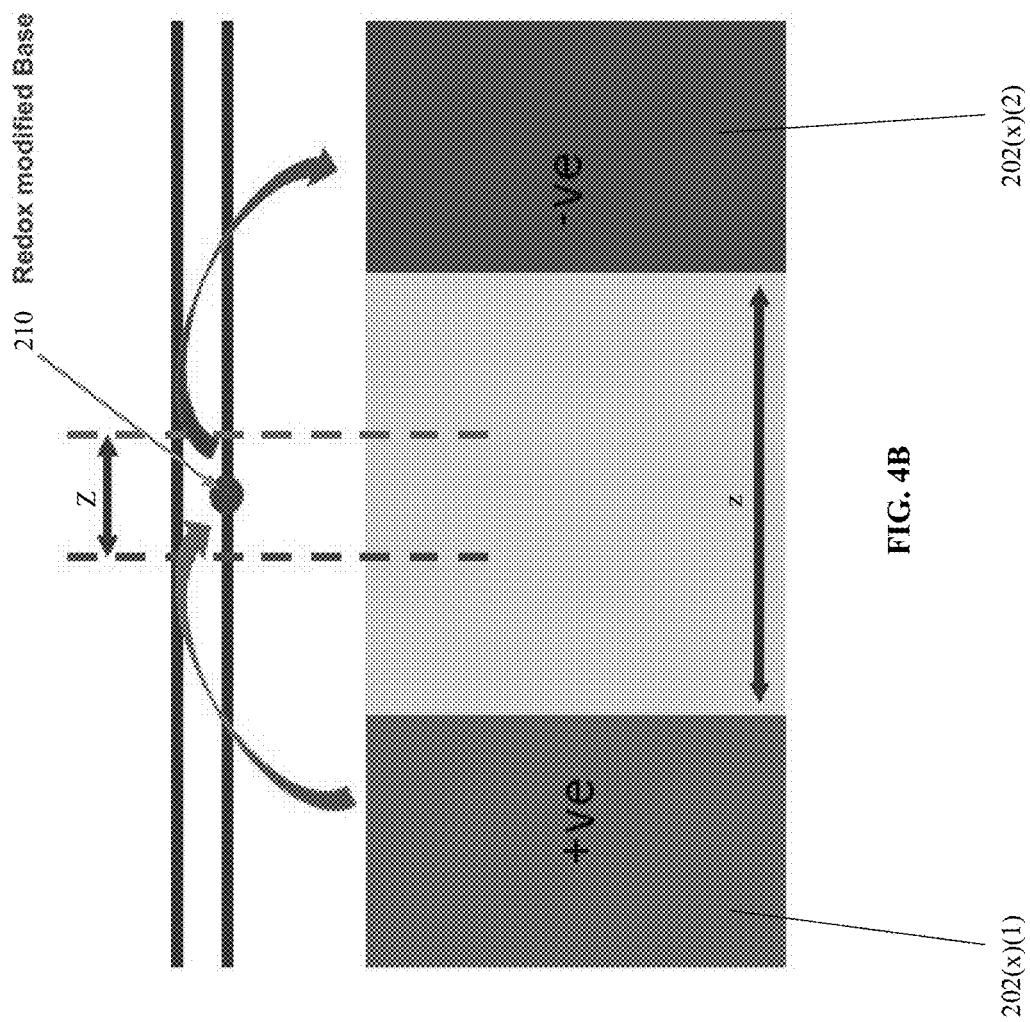
FIG. 4B illustrates a schematic of the electron shuttle according to the alternative example embodiment of the present invention.
Figure 4C:
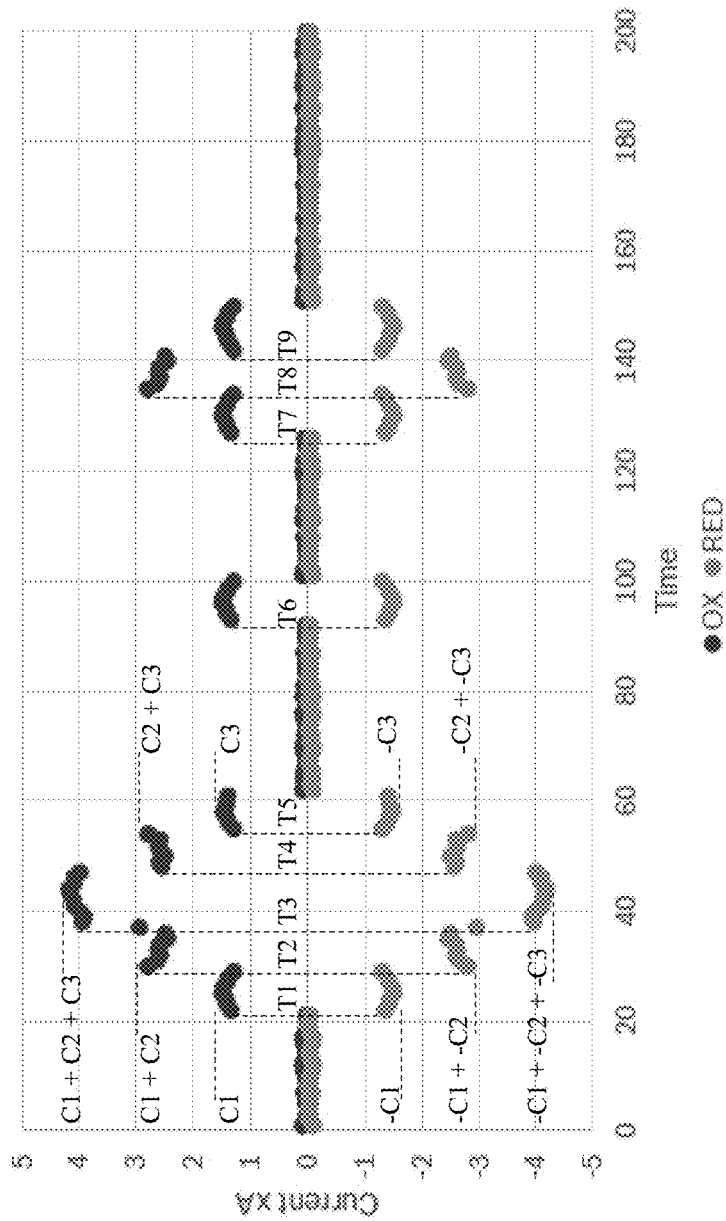
FIG. 4C illustrates the differential signals obtained from a device according to the alternative example embodiments of the present invention.

As shown in FIG. 4B, first electrode 202(x)(1) can be held at an oxidizing bias and thus can oxidize a redox species incorporated into redox modified base 210 that comes within proximity, and second electrode 202(x)(2) can be held at a reducing bias and thus can reduce a redox species incorporated into redox modified base 210 that comes within proximity. Above insulating layer z, which separates first electrode 202(x)(1) and second electrode 202(x)(2), is sensing zone Z. Within sensing zone Z, the redox species of redox modified base 210 can be oxidized by first electrode 202(x)(1) and lose an electron, and be reduced by second electrode 202(x)(2) and gain an electron, thus becoming an electron shuttle between second electrode 202(x)(2) and first electrode 202(x)(1). As shown in FIG. 4C, the simultaneous oxidation and reduction of the redox species of redox modified base 210 while in sensing zone Z creates a differential signal. According to an example embodiment, this differential signal is amplified and/or detected. According to an example embodiment, insulating layer z is large enough to prevent shuttling of electrons in the absence of a redox species within electrode pair 202(x) between first electrode 202(x)(1) and second electrodes 202(x)(2).

As each redox modified nucleotide base 210 of strand of DNA 208 passes over each of edge electrode pairs 202, a differential signal is generated as a redox chemical reaction occurs between the redox modified nucleotide base 210 and edge electrode pair 202. This embodiment, where electrode pairs are provided, can provide a better sensor signal than the embodiment in which single electrodes are provided, because, in part, the differential signal is a much stronger indication than the non-differential signal provided by a single electrode. Moreover, the differential signal is beneficial because the noise from the two electrodes in the electrode pair will be the same, and thus can be cancelled out when looking at the differential signal. Further, with electrode pairs, the shuttling of electrons between electrodes will amplify the current passing between the electrodes. According to an example embodiment, use of multiple electrodes spaced at regular distances allows strand of DNA 208 to be probed multiple times, and because the space between nucleotide bases is well characterized, the resulting signals can be overlaid and averaged to improve accuracy. According to an example embodiment, the speed of translocation of strand of DNA 208 across edge electrode pairs 202 is uniform, and is slow enough to generate a readable signal, and fast enough to ensure a rapid DNA sequencing test. According to an example embodiment, the speed of translocation of strand of DNA 208 is determined by the first two edge electrode pairs 202(1) and 202(2). According to an example embodiment, strand of DNA 208 can be linearized by confining it into a nanochannel, by using hydrodynamic forces, by a pore technique to pull strand of DNA 208 close to the surface, or by using electrical charge-based methods to attract or repel strand of DNA 208 to or from the nanochannel wall such that it traverses the nanochannel close to the surface where edge electrode pairs 202 are located.

In an example embodiment, more than one redox modified base 210 (and thus more than one redox species) can be in sensing zone Z at the same time. For example, as shown in FIG. 4C, at time T1, a first redox modified base enters sensing zone Z and is simultaneously oxidized by positive first electrode 202(x)(1) (thereby generating current C1) and reduced by negative second electrode 202(x)(2) (thereby generating corresponding current −C1). At time T2, while the first redox modified base is still in sensing zone Z, a second redox modified base enters sensing zone Z and is simultaneously oxidized by positive first electrode 202(x)(1) (thereby generating current C2 and an overall current equal to C1 plus C2) and reduced by negative second electrode 202(x)(2) (thereby generating corresponding current −C2 and an overall current equal to −C1 plus −C2). At time T3, while the first and second redox modified bases are still in sensing zone Z, a third redox modified base enters sensing zone Z and is simultaneously oxidized by positive first electrode 202(x)(1) (thereby generating current C3 and an overall current equal to C1 plus C2 plus C3) and reduced by negative second electrode 202(x)(2) (thereby generating corresponding current −C3 and an overall current equal to −C1 plus −C2 plus −C3). At time T4, the first redox modified base leaves sensing zone Z while the second and third redox modified bases remain in sensing zone Z, resulting in a drop in the overall current generated such that the overall current from oxidation is now equal to C2 plus C3, and the overall current from reduction is now equal to −C2 plus −C3. At time T5, the second redox modified base leaves sensing zone Z while the third redox modified base remains in sensing zone Z, resulting in another drop in overall current such that the overall current from oxidation is now equal to C3, and the overall current from reduction is now equal to −C3. No more redox modified bases enter sensing zone Z until time T6, where a fourth modified base enters sensing zone Z. After that, no more redox modified bases enter sensing zone Z until time T7, when a fifth modified base enters sensing zone Z, and at time T8, when a sixth modified base enters sensing zone Z while the fifth modified base remains in sensing zone Z. At time T9, the fifth modified base leaves sensing zone Z, leaving the sixth modified base in sensing zone Z.

According to an example embodiment, sensing zone Z is small enough to sense only a small number of redox modified bases at the same time, and large enough to correct for non-linearity effects from the stretching of DNA.

According to an example embodiment, as shown in FIGS. 5A-5I, the fabrication of a device with an electrode pair is as follows:

A 300 nm $SiO_2$ layer is deposited on a silicon substrate as a mask layer and patterned by photolithography and subsequently etched with buffered HF.

Figure 5A:
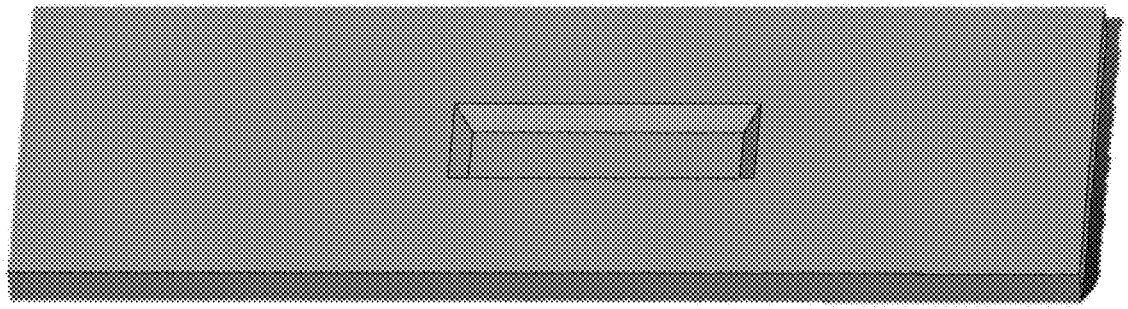
FIGS. 5A-5I illustrate the fabrication of a device, according to an example embodiment of the present invention.

A trench is wet etched into silicon substrate using KOH etchant to form the structure shown in FIG. 5A.

A barrier layer of 300 nm $SiO_2$ is deposited over the silicon substrate.

Figure 5B:
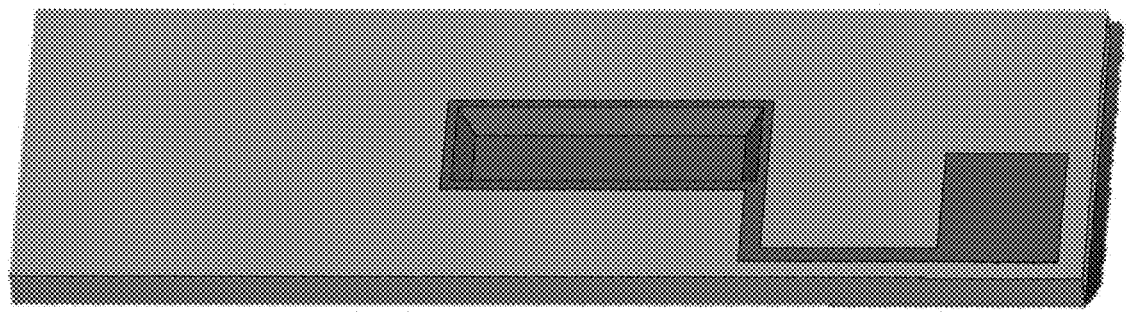

A resist is spin coated and photolithographically patterned, followed by deposition of a first electrode layer on the silicon substrate, followed by lift off to form the structure shown in FIG. 5B.

Optionally, depending on the electrode material, an adhesion layer is included between the silicon substrate and the first electrode layer.

Figure 5C:
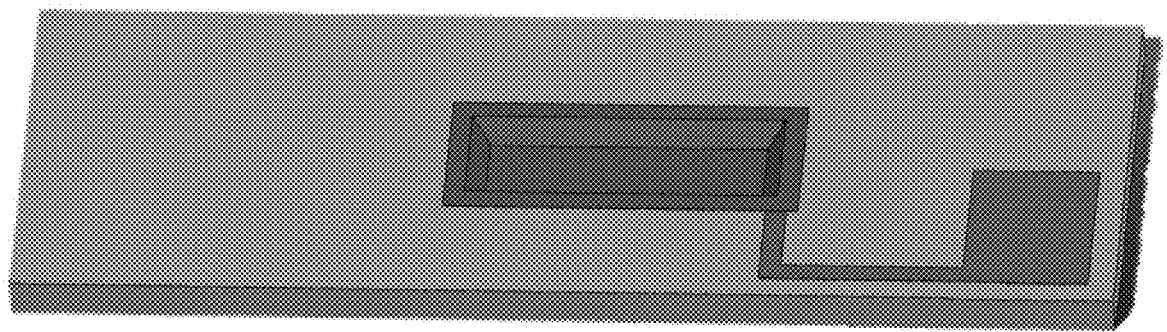

An ALD dielectric layer is deposited on the first electrode layer, which corresponds to the insulating layer z, and can be about 0.1 to about 10 nanometer thick to form the structure shown in FIG. 5C.

Figure 5D:
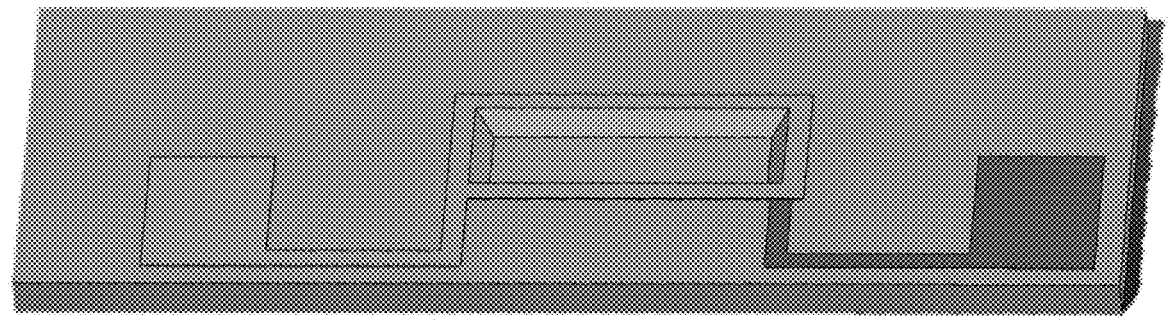

A second electrode layer is deposited on the dielectric layer to form the structure shown in FIG. 5D, each of the electrode layers including a respective electrode pad, e.g., as shown.

Figure 5E:
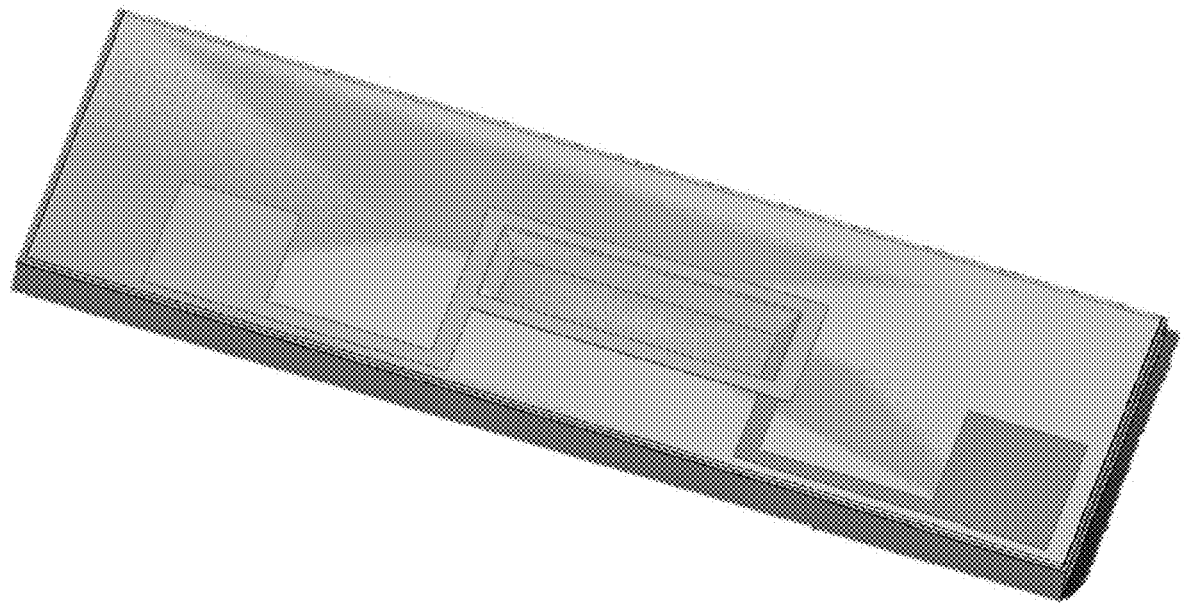

The substrate is then planarized (for example, using spin-on-glass process) to fill the trench and obtain a flat surface, to form the structure shown in FIG. 5E.

Figure 5F:
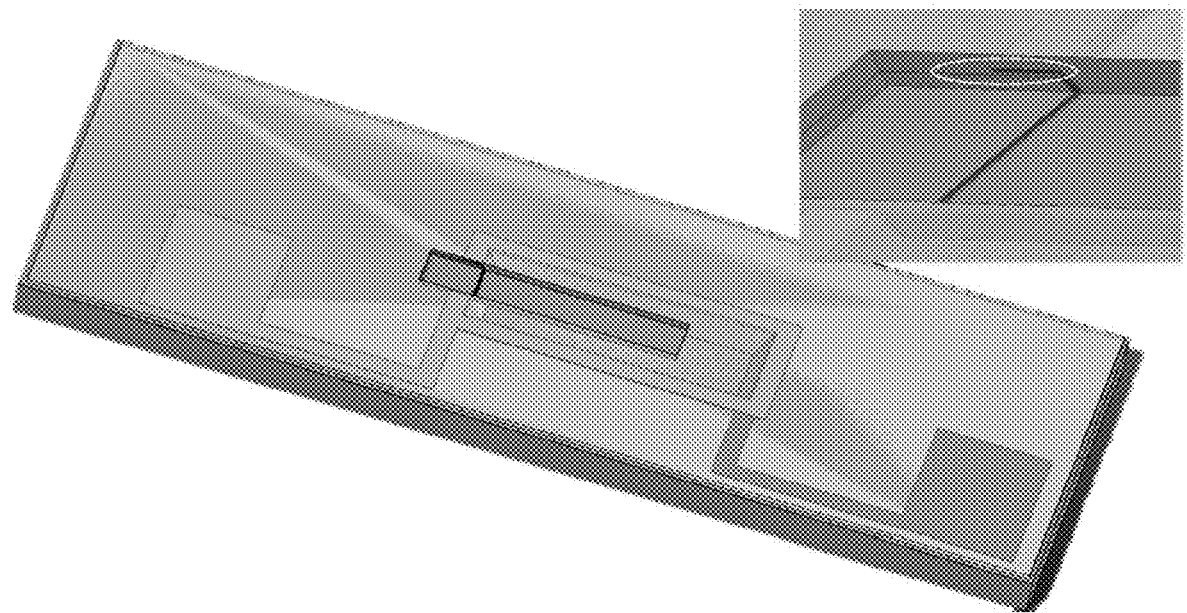

A window is etched to expose the electrode set (i.e., the first electrode, insulating layer, and the second electrode) at the bottom of the etched window, but an electrode set is also exposed at the sidewall of the etched window, forming the structure shown in FIG. 5F.

Figure 5G:
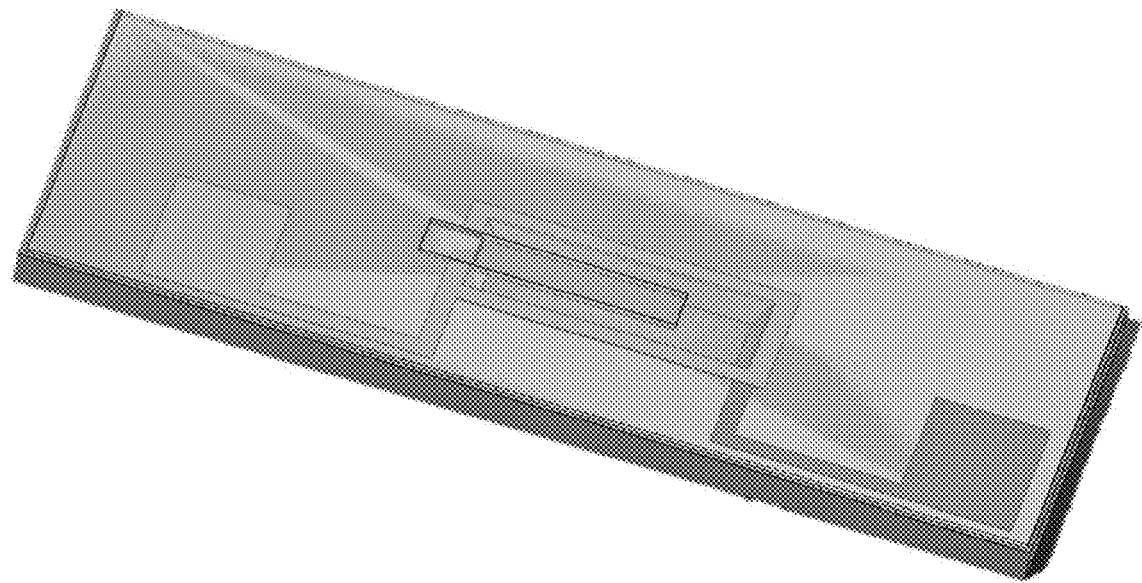

The substrate is then planarized again (for example, using spin-on-glass process) to fill in the etched regions and obtain a flat surface, thereby forming a structure as shown in FIG. 5G.

Figure 5H:
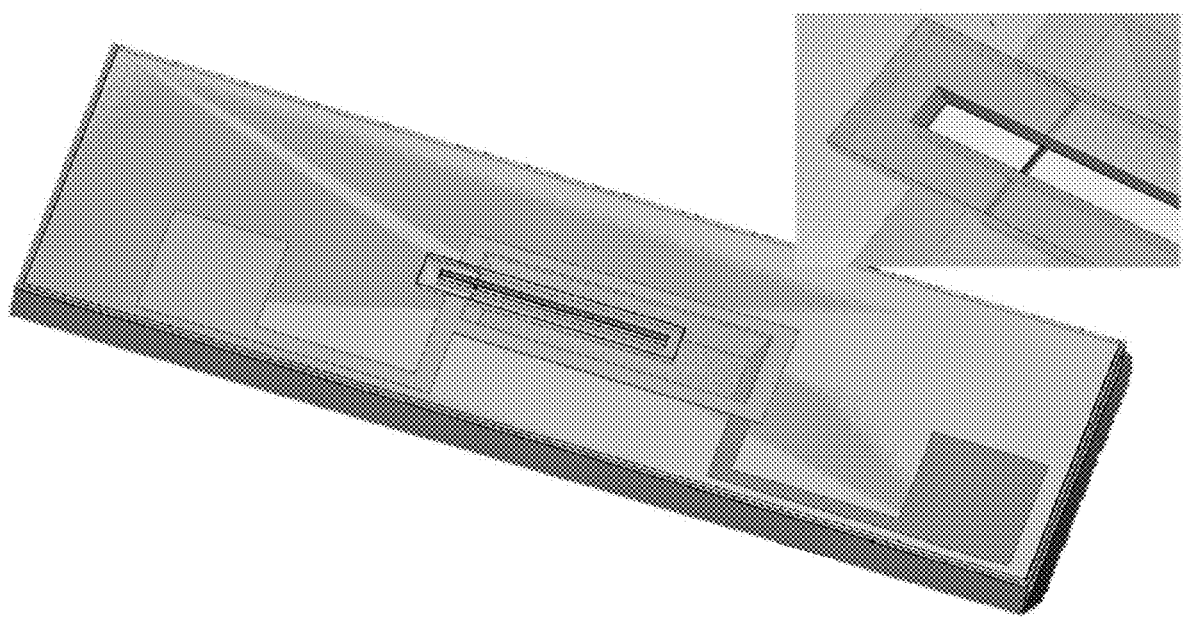

A second, smaller window is etched to form a channel through which a DNA strand can pass for sequencing, thereby forming the structure as shown in FIG. 5H.

Figure 5I:
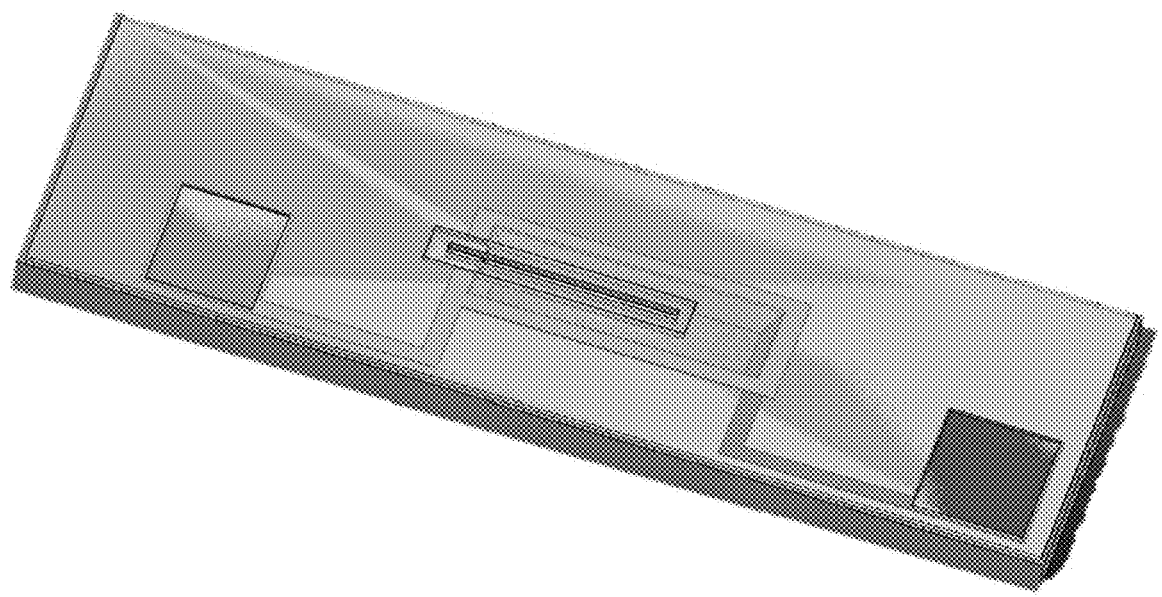

Windows are also open to the electrode pads or contacts to for electrically contacting and controlling the electrodes, thereby forming the structure shown in FIG. 5I.

Figure 6A:
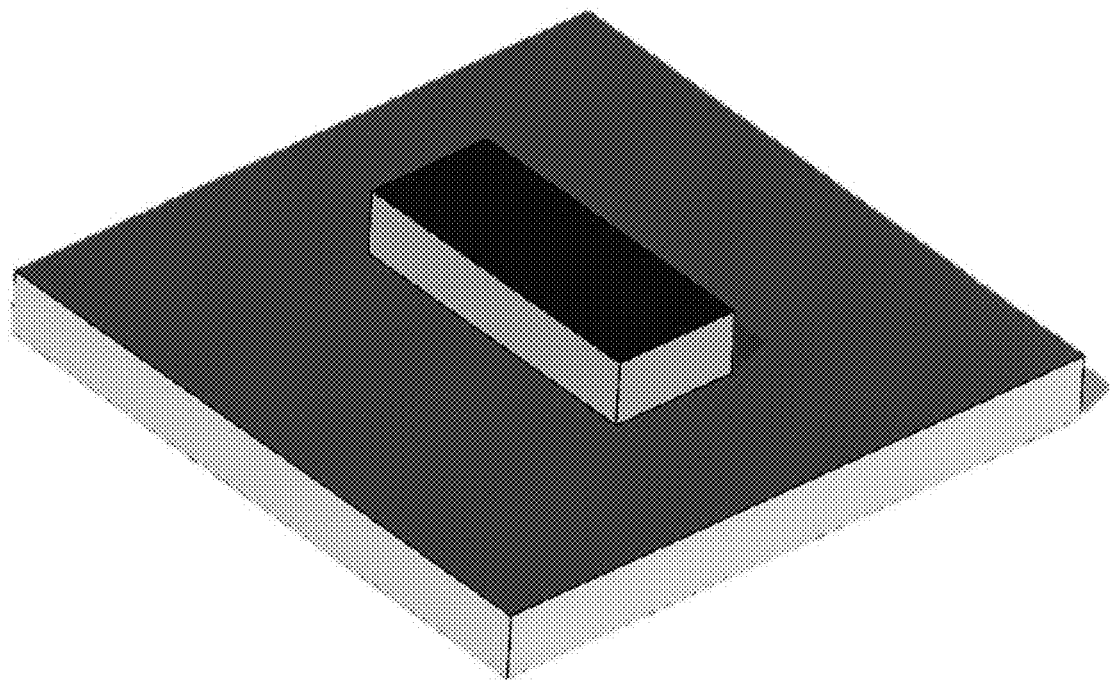
FIGS. 6A-6G illustrate the fabrication of the device, according to an alternative example embodiment of the present invention.

According to an example embodiment, as shown in FIGS. 6A-6G, the fabrication of a device with an electrode pair, according to an alternative example embodiment, is as follows:

Starting with a block of silicon substrate, the block is either etched down to form a pillar of silicon in the center of the block, or a layer of silicon oxide is grown on top of the silicon block to form a pillar of silicon oxide in the center of the block, thereby forming the structure shown in FIG. 6A. The pillar can be about 1-20 micrometers in diameter, and about 1 micrometer high.

A barrier layer of 300 nm $SiO_2$ is deposited over the silicon substrate.

Figure 6B:
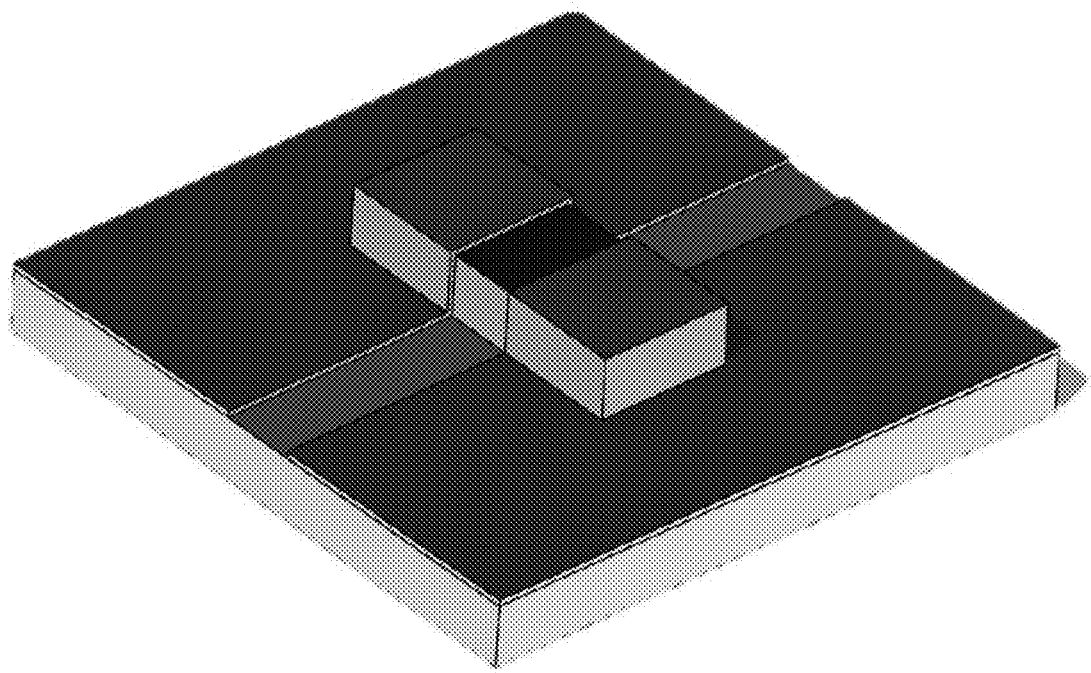

A resist is spin coated and photolithographically patterned, followed by deposition of a first electrode layer on the substrate, with an exposed strip across the middle of the substrate, where the layer can be about 100 nanometers thick, thereby forming the structure shown in FIG. 6B.

Figure 6C:
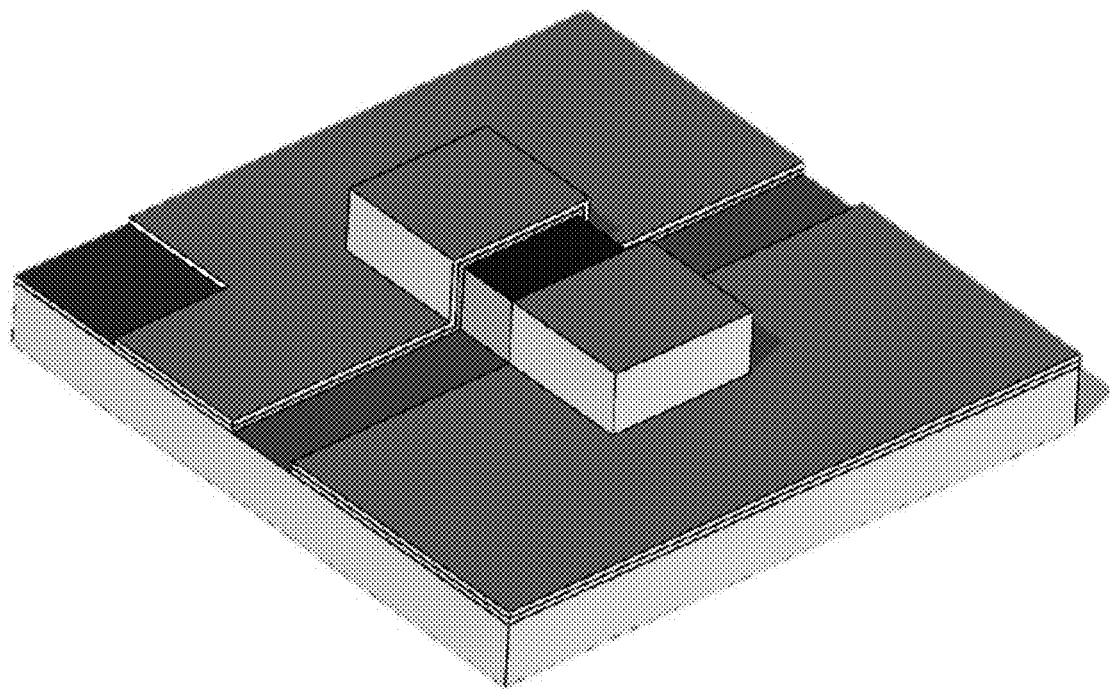

An ALD dielectric layer, which corresponds to insulating layer z and is, in an example, about 0.1 to about 10 nanometer thick, is then deposited, with the strip remaining exposed and with a portion of the underlying first electrode layer being exposed to form the electrode contact or pad, thereby forming the structure shown in FIG. 6C.

Figure 6D:
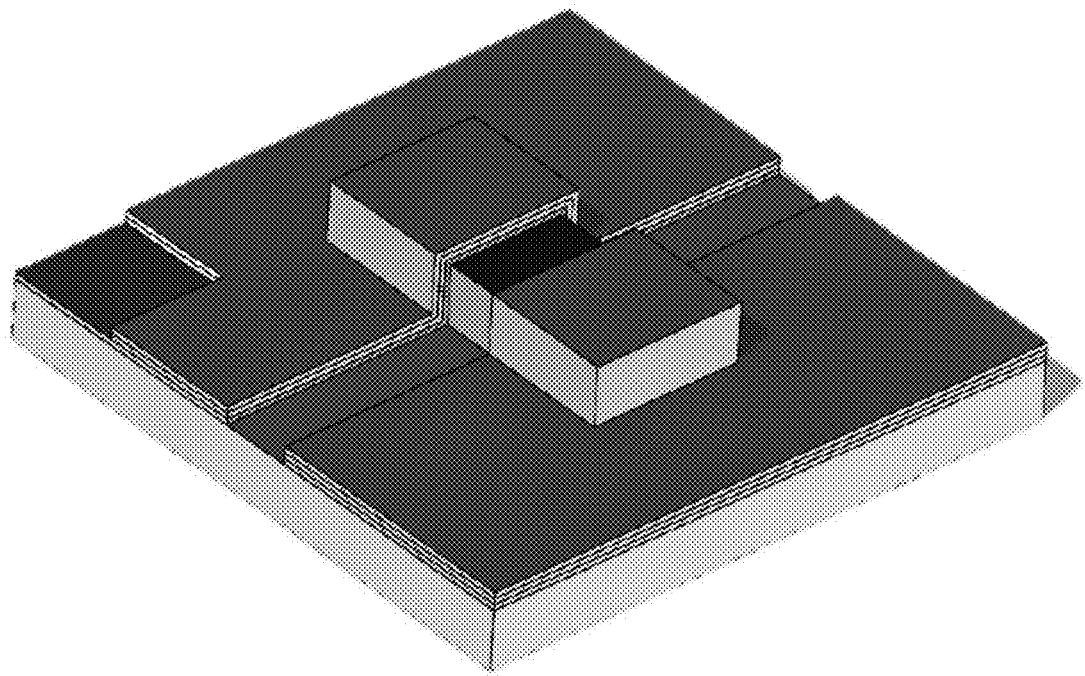

A second electrode layer, e.g., of approximately 100 nanometers thickness, is then deposited, leaving the strip exposed and leaving the contact/pad of the first electrode layer exposed, thereby forming the structure shown in FIG. 6D.

Figure 6E:
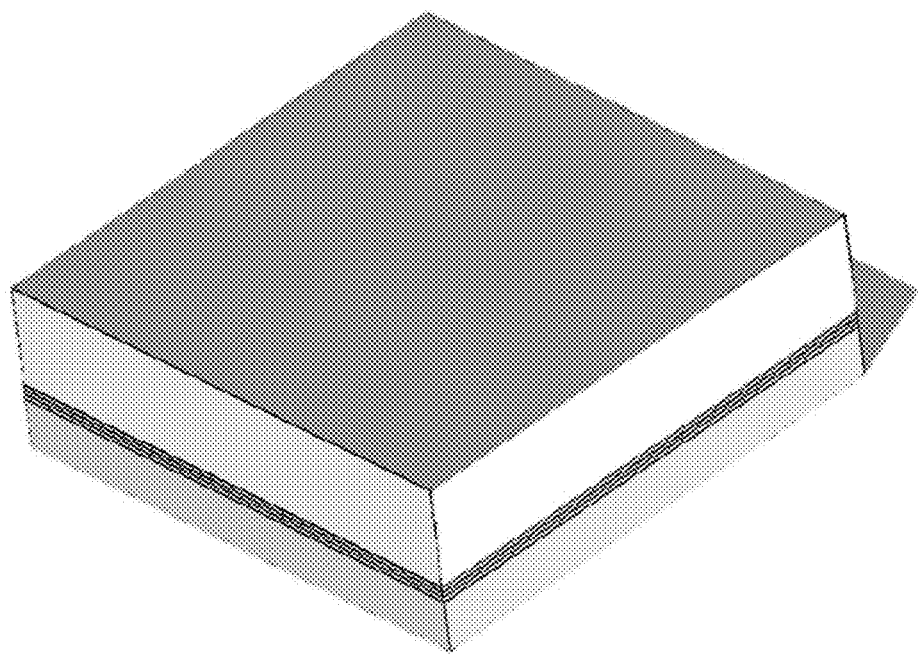

The substrate is then planarized (for example, using spin-on-glass process) to obtain a flat surface, thereby forming the structure shown in FIG. 6E.

Figure 6F:
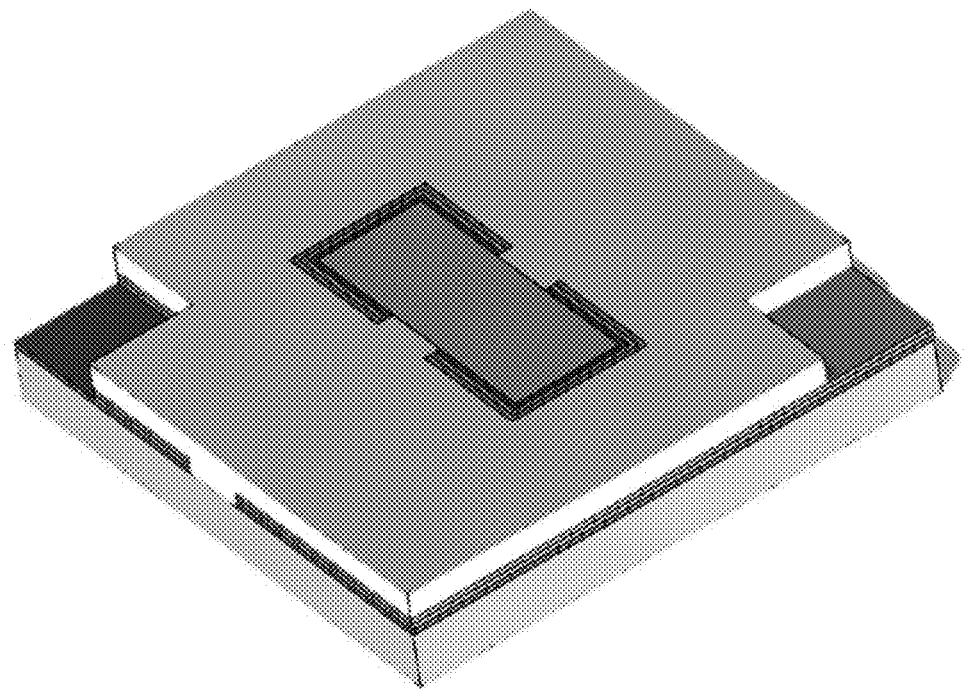

The substrate, electrode layers, and ALD layer are then exposed by etching, polishing, or lapping down of the spin-on-glass, the etching, polishing, or lapping down being performed to a greater extent at pad/contact locations, e.g., at corners, to expose the respective electrode contacts or pads of the respective electrode layers, thereby forming the structure shown in FIG. 6F.

Figure 6G:
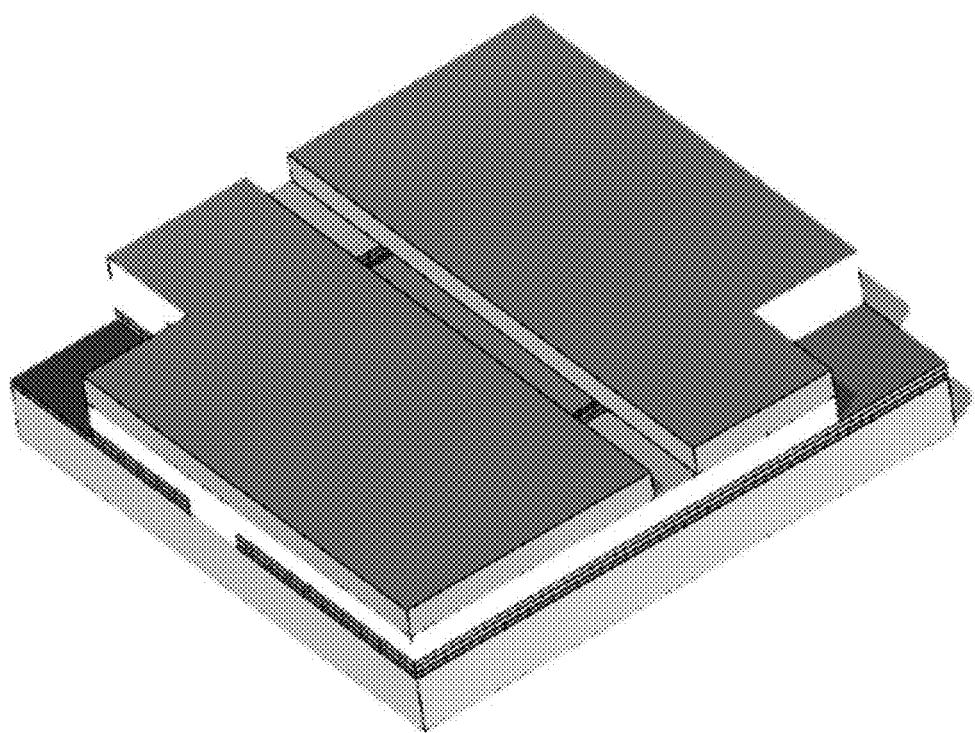

A nanochannel is created, by sputtering and etching, by photolithography, or by soft lithography, thereby forming the structure shown in FIG. 6G.

Figure 7:
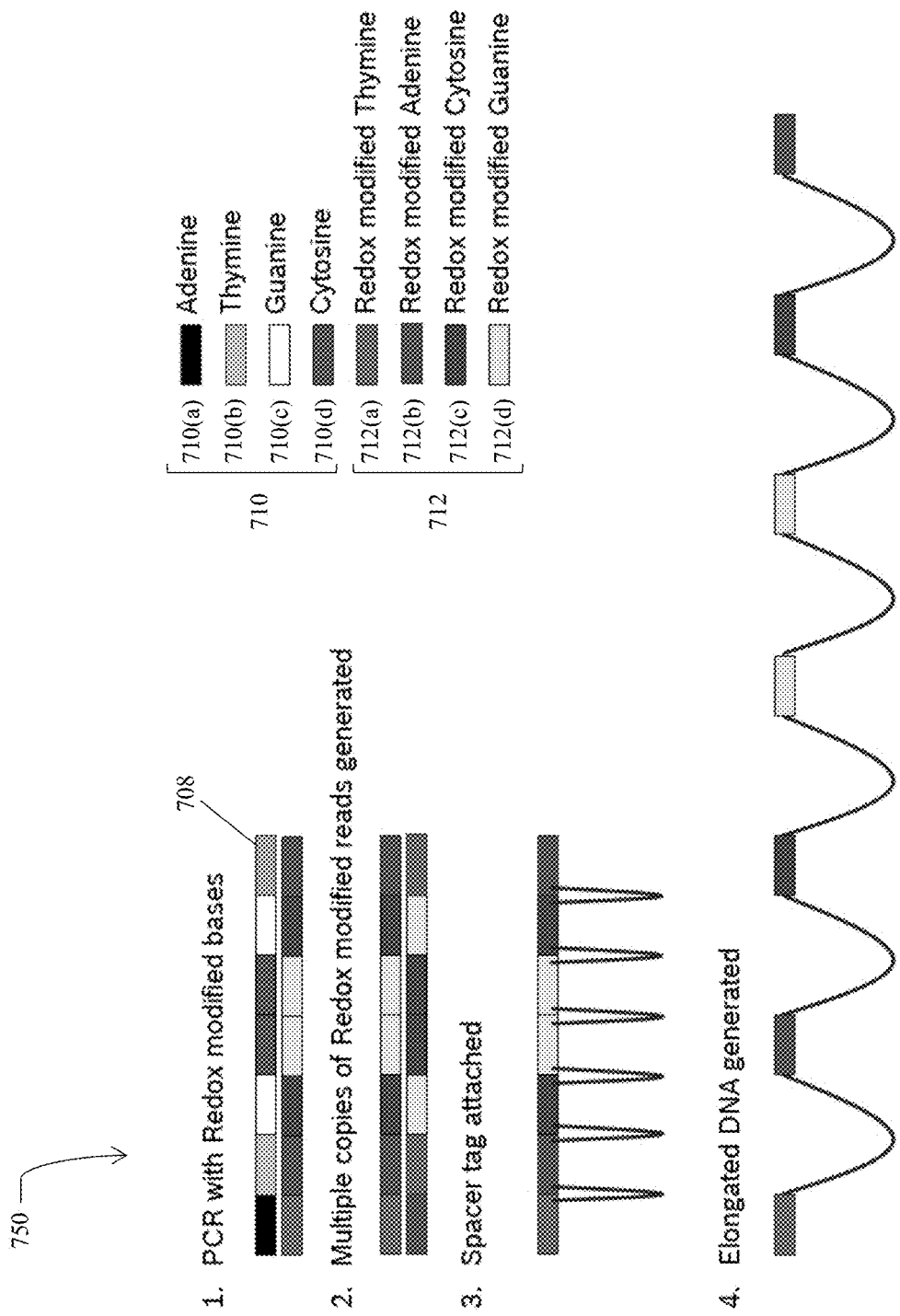
FIG. 7 illustrates a schematic of steps for a 1 pot DNA sequencing method, according to an example embodiment of the present invention.
Figure 8:
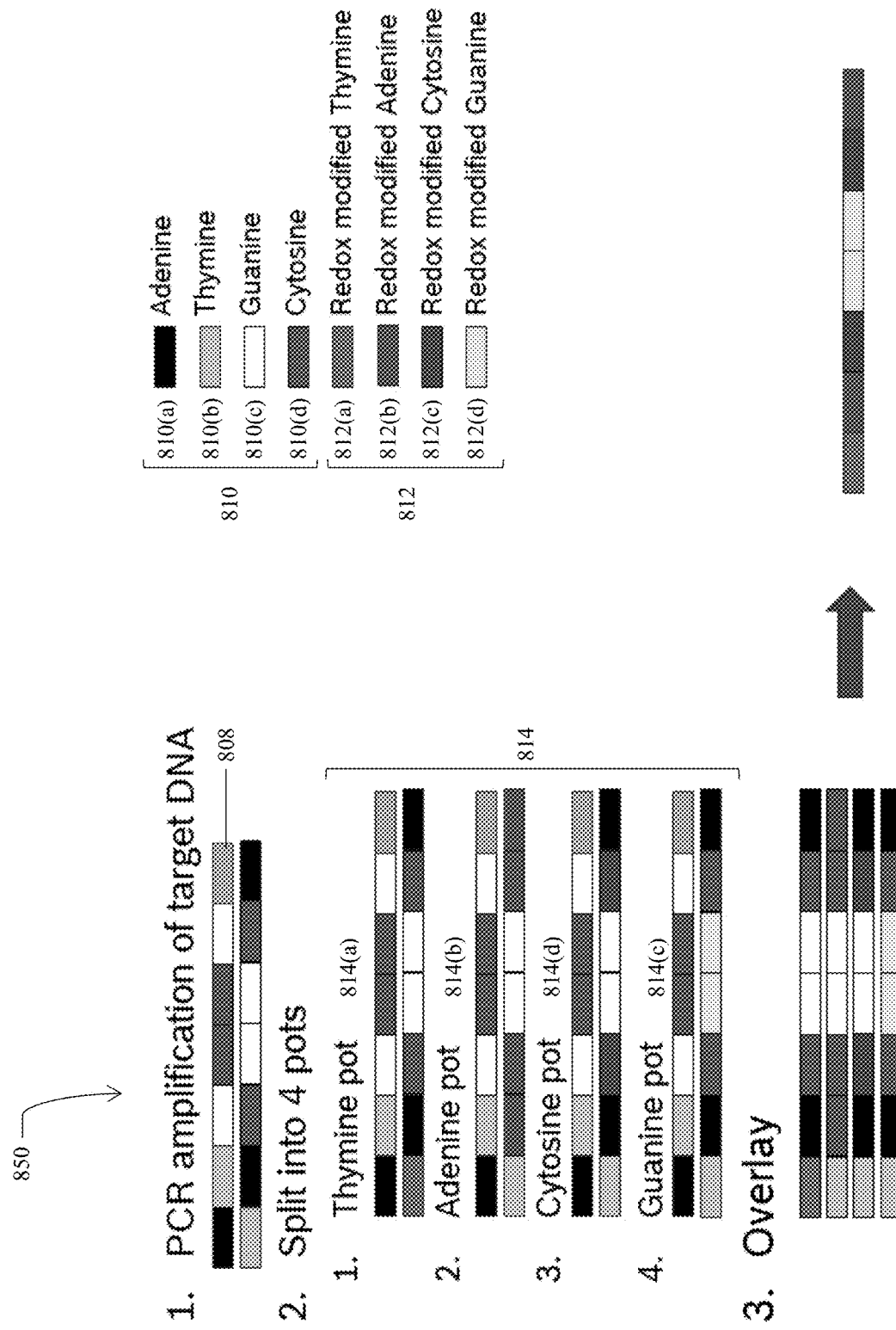
FIG. 8 illustrates a schematic of steps for a multi-pot DNA sequencing methods, according to an example embodiment of the present invention.

How a strand of DNA is replicated to incorporate redox-modified nucleotides can depend on the method of readout. FIGS. 7 and 8 illustrate two different methods to generate the same outcome by changing the way the redox species are incorporated into the target strand of DNA and how the DNA is read out. FIG. 7 illustrates a 1 pot method 750, according to an example embodiment, where each nucleotide base 710 (adenine 710(a), thymine 710(b), guanine 710(c), and cytosine 710(d)) of target strand of DNA 708 is modified with a unique redox species specific to that base 710, resulting in redox modified bases 712 (712(a), 712(b), 712(c), and 712(d)). Redox modified bases 712 are incorporated into the copy strand of the DNA during PCR. By choosing electrochemical groups (for the unique redox species) that have different oxidation or reduction potential, an electrode (such as edge electrode 102) can be used to probe each redox modified nucleotide base 712 to determine at what potential oxidation or reduction takes place.

According to an example embodiment, the unique redox species is reversible within the stable window of the electrode, is biocompatible with any biochemistry in solution, and is stable under standard laboratory conditions. If multiple redox species are used, there should be sufficient difference in electrochemical response to enable differentiation between species. Examples of redox species include anthraquinone (which has an oxidation potential of 0.40 V), methylene blue (which has an oxidation potential of 0.20 V), ferrocene (which has an oxidation potential of 0.50 V), and phenothiazine (which has an oxidation potential of 0.60 V) (all potentials versus Ag/AgCl).

As the strand of DNA passes over the probing edge electrode, the nucleotide bases will be oxidized or reduced sequentially (depending on the incorporated redox species), and the current peaks as a function of probing voltage can be used to identify each passing nucleotide base and assign a base sequence to the strand of DNA.

According to an example embodiment, a single electrode can be used that sweeps the electrode voltage rapidly (akin to cyclic voltammetry), and the spike in current as a function of voltage is used to specify the redox species of interest, and thus identify the passing nucleotide base. Multiple cycles can be used to ensure enough signal is sampled to detect from the noise.

According to another example embodiment, multiple electrodes can be used, where a positive or negative bias is applied to different electrodes in the stack that sequentially changes in magnitude as the strand of DNA progresses along the stack over the electrodes. Thus, for example, a redox species with a low oxidation voltage would be excited by one electrode in the stack, while another redox species with a higher oxidation potential would only oxidize at another electrode with higher bias further down the stack.

According to an example embodiment, only three redox species are used, one for each of three of the nucleotide bases. According to an example embodiment, any gap in signal is equivalent to the last encoded base where there is sufficient DNA translocation control (i.e., a consistent time per base probing period). Methods for DNA translocation control within the literature include voltage, enzyme mediated, optical tweezers, and magnetic tweezers. See, e.g., Carson et al., "Challenges in DNA motion control and sequence readout using nanopore devices," Nanotechnology, 26(7):074004 (2015).

FIG. 8 illustrates a 4 pot method 850, according to an example embodiment. Instead of incorporating a unique redox species per each nucleotide base, target DNA strand 808 is first amplified by traditional PCR, followed by splitting the material into 4 pots 814, each pot corresponding to one group of nucleotide bases (e.g., a thymine pot 814(a), an adenine pot 814(b), a cytosine pot 814(c), and a guanine pot 814(d)). Within each pot, a second round of PCR is used to introduce a unique redox species for that pot's nucleotide base group, resulting in a group of modified nucleotide bases 812 (812(a), 812(b), 812(c), and 812(d)) while the remaining three groups of nucleotide bases 810 (810(a), 810(b), 810(c), and 810(d)) remain unmodified as standard dNTPs.

A known strand of DNA is ligated to the target/copy DNA strands to denote the zero point for base classification. The 4 pots 814 are then introduced to a device (like device 100) with at least one probing edge electrode (like edge electrode 102), and then indexed based on the known strand of DNA. According to an example embodiment, the 4 pots 814 can be sequentially introduced to the device (like device 100) with at least one probing edge electrode (like edge electrode 102). According to an example embodiment, the translocation rate over the probing edge electrode should be highly controlled to ensure that indexing can be accurate.

According to an example embodiment, the multi-pot method 850 illustrated in FIG. 8 can utilize only 2 pots due to the complementary nature of DNA strands. The first pot would correspond to either a thymine pot 814(*a*) or an adenine pot 814(*b*), and the second pot would correspond to either a cytosine pot 814(*c*) or a guanine pot 814(*d*).

In both of the methods illustrated by FIGS. 7 and 8 for electrochemically probing DNA, according to an example embodiment, a spacer region can be introduced to improve the accuracy of single base probing. As illustrated by FIG. 7, a spacer is inserted between all nucleotide bases within the DNA strand, leading to the separation of individual bases by the length of the spacer. With the redox species separated by a larger distance, the probability that the edge electrode will probe more than one redox species at a time is reduced. This also reduces the requirements for translocation accuracy, as there is a larger window of time per nucleotide base for data processing. According to an example embodiment, the spacer attaches between bases and then chemically cleaves between the bases, resulting in the cross linking of the spacer between two bases. In contrast to the disclosure in U.S. Pat. Nos. 7,939,259 and 8,324,360, according to example embodiments of the present invention, the spacer used to expand the DNA region does not include any coding correlated to the base being expanded; a nanopore is not used to probe the DNA substrate; the DNA sequence is not determined by a change in resistivity over a nanopore, but rather by a redox reaction between the electrode and the electrochemically modified base; and the DNA base chemistry uses one or more redox modifications.

The strand of DNA can be translocated across the edge electrodes or edge electrode pairs in multiple ways. As illustrated in FIG. 9A, according to an example embodiment, strand of DNA 908 can be translocated using a trapping principle. Particle 920 (such as a latex bead or a paramagnetic bead) is attached to the 5' or 3' end of strand of DNA 908, or to a complementary primer strand to strand of DNA 908, and particle 920 is used as a tether to move strand of DNA 908 within the tweezers (such as optical tweezers or magnetic tweezers), while at the same time being pulled by the electric field or hydrodynamic flow into edge sensing device 900. Possible trap types include optical trapping and magnetic trapping.

As illustrated in FIG. 9B, according to an example embodiment, strand of DNA 908 can be translocated using electrophoretic forces. Strand of DNA 908 has a negatively charged backbone. By applying a bias across nanochannel 930 containing edge electrode pairs 204(*x*), strand of DNA 908 will move towards the anode, i.e., DNA translocation counter electrode 206(*b*). By placing the anode at outlet 934 to nanochannel 930, strand of DNA 908 will be dragged through nanochannel 930, where it will be linearized.

As illustrated in FIG. 9B, according to an example embodiment, strand of DNA 908 can be translocated using electrophoretic forces coupled with topology/structuring. Nanostructures 922 can be placed within microchannel 940 upstream of nanochannel inlet 932 to slow down strand of DNA 908 as strand of DNA 908 interacts with nanostructures 922 (for example, by wrapping around or throughout them). Strand of DNA 908 will therefore travel quickly within nanochannel 930, but slower at microchannel 940, leading to a drag on strand of DNA 908 that can induce linearization (as a portion of strand of DNA 908 will be in nanochannel 930 while the other portion is still interacting with nanostructures 922 in the microchannel 940). By controlling the location of nanochannel inlet 932 relative to adjacent microchannel 940, the drag effect can also be used to help localize strand of DNA 908 to the bottom or top of nanochannel 930, e.g., FIG. 9B illustrating strand of DNA 908 being closer to the bottom of nanochannel 930. Also illustrated in FIG. 9B is electrode 950 that pushes down strand of DNA 908 in nanochannel 930.

Figure 9C:
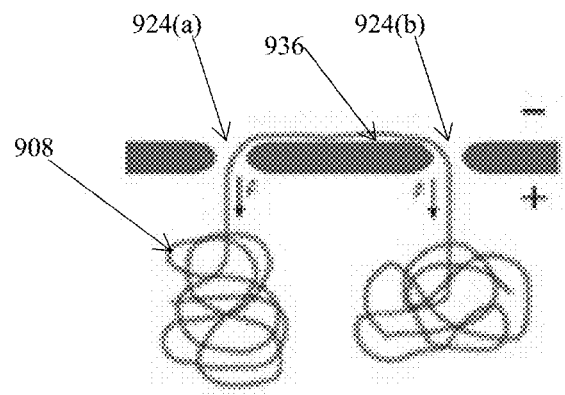

As illustrated in FIG. 9C (reproduced in part from Pud et al., *Mechanical trapping of DNA in a Double-Nanopore System*, Nano Lett. 2016, 16, 8021-8028), according to an example embodiment, another way strand of DNA 908 can be translocated using electrophoretic forces coupled with topology/structuring is the use of nanopores. Two nanopores 924(*a*) and 924(*b*) can be used to drag strand of DNA 908 across surface 936 of edge electrodes and edge electrode pairs. Strand of DNA 908 can be dragged through both nanopores 924(*a*) and 924(*b*), linearizing strand of DNA 908 and simultaneously keeping it close to surface 936.

Figure 9D:
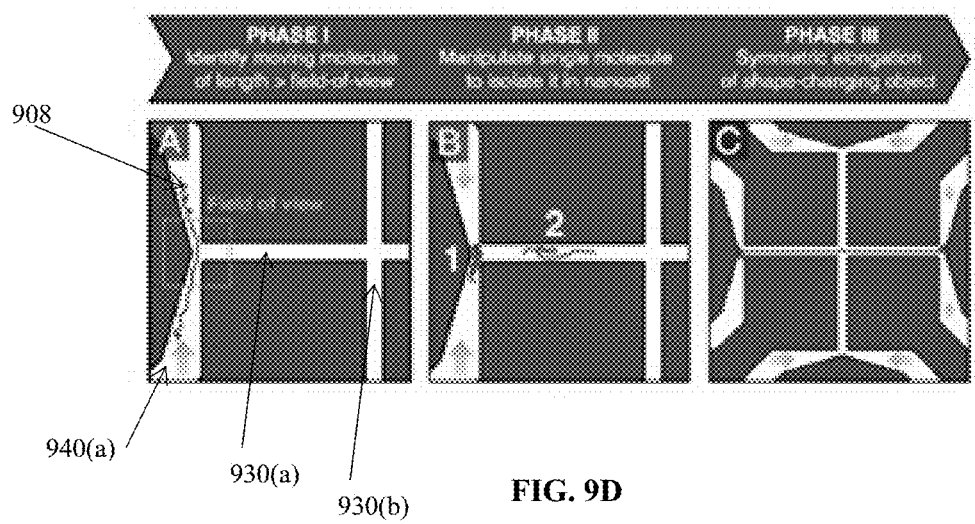

As illustrated in FIG. 9D (reproduced in part from Sorensen et al., *Automation of a single-DNA molecule stretching device*, Review of Scientific Instruments, 2015 86:6), according to an example embodiment, strand of DNA 908 can be translocated using pressure driven flow. Strand of DNA 908 is introduced into first nanochannel 930(*a*) via microchannel 940(*a*) adjacent to inlet 932(*a*). Second nanochannel 930(*b*) intersects first nanochannel 930(*a*), running perpendicular at the center of first nanochannel 930(*a*). When strand of DNA 908 reaches the center of first nanochannel 930(*a*), the flow rate in the channels can be changed to alter the pressure in the channels. This pressure differential across first nanochannel 930(*a*) leads to hydrodynamic shearing that can linearize strand of DNA 908.

The embodiments described above, which have been shown and described by way of example, and many of their advantages will be understood by the foregoing description, and it will be apparent that various changes can be made in the form, construction and arrangement of the components without departing from the disclosed subject matter or without sacrificing one or more of its advantages. Indeed, the described forms of these embodiments are merely explanatory. These embodiments are susceptible to various modifications and alternative forms, and the following listing of claims is not intended to exclude any such changes and the embodiments are not to be limited to the particular forms disclosed, but rather to cover all modifications, equivalents, and alternatives falling with the spirit and scope of this disclosure.

That is, the above description is intended to be illustrative, and not restrictive, and is provided in the context of a particular application and its requirements. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the general principles defined herein may be applied to other embodiments and applications without departing from the spirit and scope of the described embodiments, and the true scope of the embodiments and/or methods of the present invention are not be limited to the embodiments shown and described, since various modifications will become apparent to the skilled practitioner upon a study of the drawings, specification, and following claims. For example, components and functionality may be separated or combined differently than in the manner of the various described embodiments, and may be described using different terminology. These and other variations, modifications, additions, and improvements may fall within the scope of the disclosure as defined in the claims that follow.

What is claimed is:

1. A device to electrochemically sequence DNA comprising a redox species, the device comprising:
    a DNA comprising a nucleotide comprising redox species;
    at least one edge electrode;
    at least one stack of insulator material; and
    a pair of DNA translocation electrodes, that includes a DNA translocation working electrode and a DNA translocation counter electrode;
    wherein:
        a thickness of each of the at least one edge electrode is about 0.5 nanometers;
        a thickness of each of the at least one stack of insulator material is about 10 nanometers; and
        the device defines a channel configured to contain the DNA comprising a redox species, the channel being defined by one or more side wall(s) along the length of the channel, where at least a first portion of one or more of the side wall(s) comprises the at least one edge electrode and at least a second portion of one or more of the side wall(s) comprises no edge electrode along the full length of the channel.

2. The device of claim 1, wherein:
    the at least one edge electrode includes 1 to 50 edge electrodes and the at least one stack of insulator material includes 2 to 50 stacks of insulator material;
    the edge electrodes and stacks of insulator material alternate; and
    a total thickness of the edge electrodes and stacks of insulator material is about 20 nanometers to about 1000 nanometers.

3. The device of claim 1, wherein the at least one edge electrode comprises a conductive material, and the insulator material comprises a dielectric material.

4. The device of claim 3, wherein the at least one edge electrode is titanium nitride or platinum, and the insulator material is selected from the group consisting of silicon dioxide, silicon nitride, and aluminum oxide.

5. The device of claim 4, wherein the at least one edge electrode comprises a nanoscale planar electrode edge structure.

6. A device to electrochemically sequence DNA comprising a redox species, the device comprising:
    a DNA comprising a nucleotide comprising redox species;
    at least one pair of edge electrodes, that includes a first electrode held at an oxidizing bias and a second electrode held at a reducing bias;
    at least one stack of insulator material; and
    a pair of DNA translocation electrodes, that includes a DNA translocation working electrode and a DNA translocation counter electrode;
    wherein:
        the first electrode and the second electrode are separated by an insulating layer;
        above the insulating layer is a sensing zone;
        the first electrode is configured to oxidize a redox species that is in the sensing zone while the second electrode reduces the redox species; and
        the device defines a channel configured to contain the DNA comprising a redox species, the channel being defined by one or more side wall(s) along the length of the channel, where at least a first portion of one or more of the side wall(s) comprises the at least one pair of edge electrodes and at least a second portion of one or more of the side wall(s) comprises no edge electrode along the full length of the channel.

7. The device of claim 6, wherein the at least one pair of edge electrodes includes a plurality of pairs of edge electrodes, and at least any two pairs of edge electrodes are configured to measure or set a speed of translocation of the DNA across the multiple pairs of edge electrodes.

8. The device of claim 7, wherein the speed of translocation of the DNA across the multiple pairs of edge electrodes is uniform or the speed of translocation of the DNA across the multiple pairs of edge electrodes changes at a constant rate.

9. The device of claim 7, wherein a thickness of at least one of the edge electrodes is 50 nm or greater.

10. A method of electrochemically sequencing a strand of DNA, the method comprising:
    modifying each nucleotide of at least two nucleotide base groups of the strand of DNA to incorporate a redox species, including (a) modification of each nucleotide of a first nucleotide base group to incorporate a first redox species having a first oxidation or reduction potential, and (b) modification of each nucleotide of a second nucleotide base group to incorporate a second redox species having a second oxidation or reduction potential;
    applying a voltage to at least one edge electrode;
    passing the strand of DNA over the at least one edge electrode;
    oxidizing or reducing, using the at least one edge electrode, each modified nucleotide as the respective modified nucleotide passes over the at least one edge electrode, wherein the oxidizing or reducing generates an electrochemical signal that includes a change in current;
    identifying each modified nucleotide based on the electrochemical signal; and
    determining a sequence of the strand of DNA.

11. The method of claim 10, wherein:
    the first and second nucleotide base groups are different than each other; and
    the first and second nucleotide base groups are not complementary to each other.

12. The method of claim 10, further comprising incorporating the redox modified nucleotides using polymerase chain reaction, multiple displacement amplification, or isothermal amplification.

13. The method of claim 10, further comprising inserting a spacer between adjacent nucleotides of the strand of DNA.

14. The method of claim 10, wherein the applying of the voltage to the at least one edge electrode includes cycling the voltage between an oxidation potential and a reducing potential.

15. The method of claim 10, wherein each modified nucleotide is oxidized or reduced multiple times as the respective modified nucleotide passes over the at least one edge electrode.

16. The method of claim 10, further comprising passing the strand of DNA over multiple edge electrodes that are spaced at regular distances in parallel, wherein the sequence of the strand of DNA is determined multiple times using each of the edge electrodes.

17. A method of electrochemically sequencing a strand of DNA, the method comprising:
    modifying each nucleotide of the strand of DNA to incorporate a redox species, wherein each modified nucleotide in a first group consists of a first nucleotide base, and each modified nucleotide in a second group consists of a second nucleotide base;
    applying a voltage to at least one edge electrode;
    passing the modified strands of DNA over the at least one edge electrode;
    oxidizing or reducing, using the at least one edge electrode, each modified nucleotide as the respective modified nucleotide passes over the at least one edge electrode, wherein the oxidizing or reducing generates an electrochemical signal that includes a change in current;
    overlaying the electrochemical signals generated from each strand of DNA;
    identifying each modified nucleotide; and
    determining a sequence of the strand of DNA;
    wherein:
        the modifying includes (a) modification of each nucleotide of the first group to incorporate the redox species, (b) modification of each nucleotide of the second group to incorporate the redox species; and
        the first and second nucleotide bases are different and non-complementary.

18. The method of claim 17, further comprising amplifying the strand of DNA prior to modifying each nucleotide of the strand of DNA to incorporate a redox species.

19. The method of claim 18, further comprising ligating a known strand of DNA to each of the amplified strands of DNA.

20. The method of claim 17, further comprising introducing a spacer between adjacent nucleotides of each amplified strand of DNA.

21. The method of claim 17, wherein each modified nucleotide in the first group is either a redox modified Adenine or Thymine deoxynucleoside triphosphate (dNTP), and each modified nucleotide in the second group is either a redox modified Cytosine or Guanine dNTP.

* * * * *